United States Patent
Nakamura et al.

(10) Patent No.: US 11,302,425 B2
(45) Date of Patent: Apr. 12, 2022

(54) TEST SERVER, COMMUNICATION TERMINAL, TEST SYSTEM, AND TEST METHOD

(71) Applicant: SONY CORPORATION, Tokyo (JP)

(72) Inventors: Tomohiko Nakamura, Tokyo (JP); Naoki Morimoto, Tokyo (JP)

(73) Assignee: SONY CORPORATION, Tokyo (JP)

( * ) Notice: Subject to any disclaimer, the term of this patent is extended or adjusted under 35 U.S.C. 154(b) by 1103 days.

(21) Appl. No.: 15/103,958

(22) PCT Filed: Nov. 18, 2014

(86) PCT No.: PCT/JP2014/005778
§ 371 (c)(1),
(2) Date: Jun. 13, 2016

(87) PCT Pub. No.: WO2015/097977
PCT Pub. Date: Jul. 2, 2015

(65) Prior Publication Data
US 2016/0314254 A1   Oct. 27, 2016

(30) Foreign Application Priority Data

Dec. 24, 2013   (JP) .............................. JP2013-265133

(51) Int. Cl.
*G16H 40/67* (2018.01)
*G16H 10/40* (2018.01)
(Continued)

(52) U.S. Cl.
CPC ............. *G16H 10/40* (2018.01); *G16H 10/60* (2018.01); *G16H 40/67* (2018.01); *G16H 70/60* (2018.01); *G16H 50/20* (2018.01); *G16H 50/70* (2018.01)

(58) Field of Classification Search
None
See application file for complete search history.

(56) References Cited

U.S. PATENT DOCUMENTS

2004/0059215 A1 * 3/2004 Nishimura ............. G16H 15/00
600/410
2006/0059015 A1 * 3/2006 Van Kalken ........... G16H 10/60
705/2
(Continued)

FOREIGN PATENT DOCUMENTS

JP   2002-117139 A   4/2002
JP   2003-263507 A   9/2003
(Continued)

OTHER PUBLICATIONS

Alba, Davey; "This Device Diagnoses Hundreds of Diseases Using a Single Drop of Blood;" Nov. 10, 2014; WIRED, 4 pages https://www.wired.com/2014/11/device-diagnoses-hundreds-diseases-using-single-drop-blood/(Year: 2014).*

(Continued)

*Primary Examiner* — Rachel L. Porter
(74) *Attorney, Agent, or Firm* — Chip Law Group

(57) ABSTRACT

A test server includes: a communication unit that communicates with a plurality of communication terminals via a network, the plurality of communication terminals each being connectable to a test device capable of executing a test on the presence or absence of a disease, the diagnosis being related to the test and made by a doctor; and a control unit that acquires at least one of a result of the test and the diagnosis as a test information item from each of the plurality of communication terminals via the communication unit, causes a storage unit to store the plurality of acquired test information items, performs statistical processing on the plurality of stored test information items, and causes the communication unit to return a result of the statistical processing according to a demand given from each of the communication terminals before the doctor makes a diagnosis.

15 Claims, 26 Drawing Sheets

(51) Int. Cl.
*G16H 10/60* (2018.01)
*G16H 50/70* (2018.01)
*G16H 70/60* (2018.01)
*G16H 50/20* (2018.01)

(56) References Cited

U.S. PATENT DOCUMENTS

| | | | |
|---|---|---|---|
| 2008/0021288 | A1 | 1/2008 | Bowman et al. |
| 2009/0094063 | A1 | 4/2009 | Ennett |
| 2011/0020785 | A1 | 1/2011 | Lowery, Jr. et al. |
| 2013/0316374 | A1* | 11/2013 | Penninger ........ G01N 33/57415 435/7.23 |

FOREIGN PATENT DOCUMENTS

| | | | |
|---|---|---|---|
| JP | 2006-501534 | A | 1/2006 |
| JP | 2009-005940 | A | 1/2009 |
| JP | 2009-009396 | A | 1/2009 |
| JP | 2009-095649 | A | 5/2009 |
| JP | 2011-128935 | A | 6/2011 |
| JP | 2012-508383 | A | 4/2012 |
| JP | 2013-093019 | A | 5/2013 |

OTHER PUBLICATIONS

The Japanese Journal of Clinical and Experimental Medicine, ISSN0021-4965, vol. 72, No. 9, Sep. 1995, pp. 7.
Office Action for JP Patent Application No. 2015-554514, dated Sep. 25, 2018, 03 pages of Office Action and 03 pages of English Translation.
Akiyuki Okubo, "Regarding Boundary Values", The Japanese Journal of Clinical and Experimental Medicine, vol. 72, No. 9, Sep. 1995, 2119-2123 pages.
Office Action for CN Patent Application No. 201480068700.2, dated Mar. 11, 2019, 06 pages of Office Action and 09 pages of English Translation.
Akiyuki Okubo, "Kyokaichi towa", The Japanese Journal of Clinical and Experimental Medicine, ISSN0021-4965, vol. 72, No. 9, Sep. 1995, pp. 7.
International Search report on patentability received for PCT Application No. PCT/JP2014/005778, dated Jan. 20, 2015, pp. 1.
Written Opinion received for PCT Application No. PCT/JP2014/005778, dated Jan. 20, 2015, pp. 5.
International preliminary report on patentability for PCT Application No. PCT/JP2014/005778, dated Jun. 28, 2016, 5 pages.
Anthony Kwaku Akobeng, "Understanding diagnostic tests 1 : sensitivity, specificity and predictive values", Acta Paediatrica, vol. 96, No. 3, Mar. 2007, pp. 338-341.
Anthony Kwaku Akobeng, "Understanding diagnostic tests 2: Likelihood ratios, pre- and post-test probabilities and their use in clinical practice", Acta Paediatrica, vol. 96, No. 4, Apr. 2007, pp. 487-491.
Anthony Kwaku Akobeng, "Understanding diagnostic tests 3: receiver operating characteristic curves", Acta Paediatrica, vol. 96, No. 5, May 2007, pp. 644-647.
Office Action for JP Patent Application No. 2019-002649, dated Apr. 21, 2020, 03 pages of Office Action and 04 pages of English Translation.
Akiyuki Okubo, "What Is Boundary Value? Clinical Operation and Research", The Japanese Journal of Clinical and Experimental Medicine, vol. 72, No. 9, Sep. 20, 1995, pp. 2119-2123.
Office Action for JP Patent Application No. 2020-134080, dated Sep. 14, 2021, 4 pages of Office Action and 1 pages of English Translation.
Watase, et al., "Geospatial Analysis Of Tuberculosis In Tokyo", Tokyo, Japan, vol. 81, No. 7, Jul. 15, 2006, pp. 481-485.

* cited by examiner

|  | Disease | Non-Disease | Positive $a+c$ | Positive predictive value $a/(a+c)$ | Positive rate $(a+c)/(a+b+c+d)$ |
|---|---|---|---|---|---|
| Test positive | True positive $a$ | False positive $c$ | Negative $b+d$ | Negative predictive value $d/(b+d)$ | Negative rate $(b+d)/(a+b+c+d)$ |
| Test negative | False negative $b$ | True negative $d$ | Total number $a+b+c+d$ | | |
| | Number of diseases $a+b$ | Number of non-diseases $c+d$ | | Accuracy $(a+b)/(a+b+c+d)$ | |
| | Sensitivity $a/(a+b)$ | Specificity $d/(c+d)$ | | | |
| Prevalence rate $(a+b)/(a+b+c+d)$ | | | | | |

FIG.1

| Instrument ID | Patient ID | Sample ID | Date | Address | Country | Gender | Age | Assay result | Diagnosis |
|---|---|---|---|---|---|---|---|---|---|
| | | | | | | | | | |

┌─────────────────────────────────────────┐
  │                                         │
  │  Name of disease : Influenza            │
  │                                         │
  │  Prevalence rate : 10.0%                │
  │                                         │
  │  Positive predictive value : X%         │
  │                                         │
  │  Negative predictive value : Y%         │
  │                                         │
  │  Test method : Immunochromatography  ( Test start )──26b
  │                                         │
  │     PCR method │Recommended│         ( Test start )──26b
  │                      │                  │
  └──────────────────────┼──────────────────┘
                         26a
```

FIG.27

TEST SERVER, COMMUNICATION TERMINAL, TEST SYSTEM, AND TEST METHOD

CROSS REFERENCE TO RELATED APPLICATIONS

This application is a U.S. National Phase of International Patent Application No. PCT/JP2014/005778 filed on Nov. 18, 2014, which claims priority benefit of Japanese Patent Application No. JP 2013-265133 filed in the Japan Patent Office on Dec. 24, 2013. Each of the above-referenced applications is hereby incorporated herein by reference in its entirety.

TECHNICAL FIELD

The present technology relates to a test system using statistical information, to a communication terminal and a test server that configure the test system, and to a test method used in the test system.

BACKGROUND ART

Tests performed in medical care recently have been increasingly important in carrying out treatment of patients. Many test devices, test kits, and test methods are developed for clinical tests.

A test system can also be established as a network compatible client server system.

For example, in Patent Document 1, an intelligence module 105 configured by a computer, for example, receives patient test results from a data acquisition module such as a test system 150 through a direct connection or over a network 140. The intelligence module executes a disease classification process for analyzing patient test results to determine whether a patient sample is associated with an inflammatory bowel disease or a clinical subtype thereof. The determination made by the process is then provided to a client system 130.

Patent Document 1: Japanese Patent Application Laid-open No. 2012-508383

SUMMARY OF INVENTION

Problem to be Solved by the Invention

In the above-mentioned test system, however, an analysis is just performed based on the patient test results collected from a test terminal (test system) to provide a diagnosis thereof to a client. In other words, the above-mentioned test system is not a test system that preliminarily presents, before a doctor performs a clinical test, a positive predictive value and a negative predictive value (that will be described later) of the test to the doctor, to assist the doctor to determine whether to perform or stop the test.

Further, there have been no test systems that acquire test results or diagnoses from other test terminals, which are dispersed in many countries and regions, via a network, and calculates a prevalence rate (that will be described later), a positive predictive value, and a negative predictive value for each region that are changed with time, to provide them to a doctor.

Moreover, in order to improve the degree of accuracy of the prevalence rate, it is important to obtain the extremely-huge total number of test results, but increasing the total number has been not focused on.

Furthermore, there have been no test systems that cope with spread of an infectious disease, such as pandemic.

In addition, in the above-mentioned test system, there have been various problems. For example, it is impossible to enhance the degree of accuracy of information to be offered or provide higher-value-added information, based on a larger volume of information.

In view of the circumstances as described above, it is an object of the present technology to provide a test server, a communication terminal, a test system, and a test method that improve a clinical test or treatment in various aspects such as quality and cost.

Means for Solving the Problem

In order to achieve the object described above, according to an embodiment of the present technology, there is provided a test server including: a communication unit that communicates with a plurality of communication terminals via a network, the plurality of communication terminals each being connectable to a test device capable of executing a test on the presence or absence of a disease and each being capable of inputting a diagnosis on the presence or absence of the disease, the diagnosis being related to the test and made by a doctor; and a control unit that acquires at least one of a result of the test and the diagnosis as a test information item from each of the plurality of communication terminals via the communication unit, causes a storage unit to store the plurality of acquired test information items therein, performs statistical processing on the plurality of stored test information items, and causes the communication unit to return a result of the statistical processing according to a demand given from each of the communication terminals before the doctor makes a diagnosis. It should be noted that the test device used here includes test agents in addition to an original test device.

In order to achieve the object described above, in the test server according to the embodiment of the present technology, the control unit may cause the communication unit to return at least one of a prevalence rate, a positive predictive value, and a negative predictive value that are calculated as the result of the statistical processing, based on the number of test information items in which the result of the test and the diagnosis are positive, the number of test information items in which the result of the test is negative and the diagnosis is positive, the number of test information items in which the result of the test is positive and the diagnosis is negative, and the number of test information items in which the result of the test and the diagnosis are negative, in the plurality of stored test information items.

In order to achieve the object described above, in the test server according to the embodiment of the present technology, the control unit may cause the communication unit to return the positive predictive value and the negative predictive value, in addition to the prevalence rate, the positive predictive value and the negative predictive value being calculated based on the prevalence rate, a sensitivity of the test device, and a specificity of the test device.

In order to achieve the object described above, in the test server according to the embodiment of the present technology, the control unit may acquire, from each of the communication terminals, an elapsed time from the development of a disease of a patient who is to be subjected to the test, acquire a sensitivity and a specificity that correspond to the elapsed time from the development of the disease, and calculate the positive predictive value and the negative predictive value based on the acquired sensitivity and specificity.

In order to achieve the object described above, in the test server according to the embodiment of the present technology, the control unit may cause the test device to execute various types of tests for testing the disease, the test device being connected to each of the communication terminals, acquire results of the executed various types of tests from the test device, and determine a result of the test indicating the presence or absence of the disease, based on the acquired results of the various types of tests.

In order to achieve the object described above, in the test server according to the embodiment of the present technology, the test device may be capable of executing various types of tests, and the control unit may calculate, after causing the test device to execute one of the various types of tests, posttest odds in the one test based on at least one of a positive likelihood ratio and a negative likelihood ratio on the one test, transmit the posttest odds to each of the communication terminals, and acquire information on whether a subsequent test is performed or not from each of the communication terminals.

In order to achieve the object described above, in the test server according to the embodiment of the present technology, the test information items acquired from the communication terminals may each include patient attribute information indicating an attribute of a patient who is subjected to the test, and the control unit may perform, when receiving a demand to narrow down statistical information from each of the communication terminals, the statistical processing by performing narrowing-down for test information items each having the attribute of the patient attribute information, the demand specifying any patient attribute information.

In order to achieve the object described above, in the test server according to the embodiment of the present technology, the test information items acquired from the communication terminals may each include terminal attribute information indicating an attribute of each of the communication terminals that performs the test, and the control unit may perform, when receiving a demand to narrow down statistical information from each of the communication terminals, the statistical processing by performing narrowing-down for test information items each having the attribute of the terminal attribute information, the demand specifying any terminal attribute information.

In order to achieve the object described above, in the test server according to the embodiment of the present technology, the control unit may perform weighting on the result of the statistical processing, the weighting being based on the terminal attribute information, the result of the statistical processing being calculated based on the test information items obtained by narrowing-down.

In order to achieve the object described above, in the test server according to the embodiment of the present technology, the control unit may be capable of using a positive rate instead of the prevalence rate.

In order to achieve the object described above, in the test server according to the embodiment of the present technology, the test information item may include information for identifying a method of performing the test, and the control unit may be capable of using the positive rate instead of the prevalence rate in each of the methods of performing the test for an identical disease, the positive rate being the result of the statistical processing performed on a plurality of test information items acquired by one of the methods, the method satisfying preliminarily demanded predetermined values of a sensitivity and a specificity, out of sensitivities and specificities preliminarily provided to the respective methods, the prevalence rate being the result of the statistical processing performed on each of a plurality of test information items acquired by another one of the methods.

In order to achieve the object described above, in the test server according to the embodiment of the present technology, the control unit may evaluate effectiveness of the test based on the positive predictive value, transmit an evaluation result to each of the communication terminals, and cause each of the communication terminals to present a message of recommendation or non-recommendation for the test.

In order to achieve the object described above, in the test server according to the embodiment of the present technology, the test information items acquired from the communication terminals may each include information of a region in which each of the communication terminals is located, as terminal attribute information indicating an attribute of each of the communication terminals that performs the test, and the control unit may estimate the prevalence rate in a first region in which the test is not implemented, based on prevalence rates obtained in one or more second regions that are different from the first region, and based on a factor having an influence on infection between each of the second regions and the first region.

In order to achieve the object described above, in the test server according to the embodiment of the present technology, the control unit may periodically perform the statistical processing and create history information of the prevalence rate, and predict a future prevalence rate based on the history information.

In order to achieve the object described above, in the test server according to the embodiment of the present technology, the control unit may return a result of the statistical processing acquired from outside, instead of performing the statistical processing on the plurality of stored test information items.

In order to achieve the object described above, in the test server according to the embodiment of the present technology, the control unit may transmit a list of medicines to each of the communication terminals, the medicines being based on at least one of the result of the test, the diagnosis, and the result of the statistical processing, and cause each of the communication terminals to present the list as medicines recommended for medication, or the control unit may cause each of the communication terminals to present a list of methods for the test capable of being performed in the test device, a recommendation mark indicating a method for a test recommended in the list, and a user interface for starting the test.

In order to achieve the object described above, according to an embodiment of the present technology, there is provided a communication terminal including: a communication unit that communicates with a test server via a network, the test server collecting a plurality of sets of at least one of a result of a test on the presence or absence of a disease and a diagnosis on the presence or absence of the disease as test information items, and providing a result of statistical processing performed on the plurality of collected test information items, the diagnosis being related to the test and made by a doctor; an input unit that receives an input from a user or the doctor; and a control unit that causes the communication unit to transmit a demand of the result of the statistical processing to the test server, causes a test device to execute the test, presents the result of the statistical processing and a result of the executed test to the user, the result of the statistical processing being received via the communication unit from the test server, causes the user to input the diagnosis on the executed test, using the input unit, and causes the communication unit to transmit at least one of the result of the executed test and the input diagnosis as the test information item to the test server.

In order to achieve the object described above, according to an embodiment of the present technology, there is provided a test system including: a test server; and a plurality of communication terminals, the test server including a first communication unit that communicates with the plurality of communication terminals via a network, and a first control unit that acquires at least one of a result of a test on the presence or absence of a disease and a diagnosis on the presence or absence of the disease as a test information item from each of the plurality of communication terminals via the communication unit, the diagnosis being related to the test and made by a doctor, causes a storage unit to store the plurality of acquired test information items therein, performs statistical processing on the plurality of stored test information items, and causes the communication unit to return a result of the statistical processing according to a demand given from each of the communication terminals before the doctor makes a diagnosis, the plurality of communication terminals each including a second communication unit that communicates with the test server via the network, an input unit that receives an input from a user or the doctor, and a second control unit that causes the communication unit to transmit the demand of the result of the statistical processing to the test server, causes a test device to execute the test, presents the result of the statistical processing and a result of the executed test to the user, the result of the statistical processing being received via the communication unit from the test server, causes the user to input the diagnosis on the executed test, using the input unit, and causes the communication unit to transmit at least one of the result of the executed test and the input diagnosis as the test information item to the test server.

In order to achieve the object described above, according to an embodiment of the present technology, there is provided a test method including: by a control unit, acquiring, from a plurality of communication terminals each being connectable to a test device capable of executing a test on the presence or absence of a disease and each being capable of inputting a diagnosis on the presence or absence of the disease, at least one of a result of the test and the diagnosis as a test information item via the communication unit, the diagnosis being related to the test and made by a doctor; causing a storage unit to store the plurality of acquired test information items therein; performing statistical processing on the plurality of stored test information items; and causing the communication unit to return a result of the statistical processing according to a demand given from each of the communication terminals before the doctor makes a diagnosis.

In order to achieve the object described above, according to an embodiment of the present technology, there is provided a test method including: by a control unit, causing a communication unit to transmit a demand of a result of statistical processing to a test server, the communication unit communicating with the test server via a network, the test server collecting a plurality of sets of at least one of a result of a test on the presence or absence of a disease and a diagnosis on the presence or absence of the disease as test information items, and providing the result of the statistical processing performed on the plurality of collected test information items, the diagnosis being related to the test and made by a doctor; causing the communication unit to transmit the demand of the result of the statistical processing to the test server; causing a test device to execute the test; presenting the result of the statistical processing and a result of the executed test to a user or the doctor, the result of the statistical processing being received via the communication unit from the test server; causing the user to input the diagnosis on the executed test, using an input unit that receives an input from the user; and causing the communication unit to transmit at least one of the result of the executed test and the input diagnosis as the test information item to the test server.

Effect of the Invention

As described above, according to the present technology, it is possible to improve a clinical test or treatment in various aspects such as quality and cost. It should be noted that the effects described herein are not necessarily limited, and any of the effects described herein may be produced.

BRIEF DESCRIPTION OF DRAWINGS

FIG. 1 is a diagram showing a state where a clinical test of a certain disease is performed by a certain test method.

FIG. 5 is a diagram showing an example of fields (items) in each record that configures a database 47a.

FIG. 27 is a diagram showing a specific example in which a list of test methods feasible by the test device 28 of the test terminal 20 is presented on the test terminal 20 in addition to a name of a disease, a prevalence rate, a positive predictive value, and a negative predictive value, and a recommended test method is further displayed thereon.

MODE(S) FOR CARRYING OUT THE INVENTION

Figure 2:
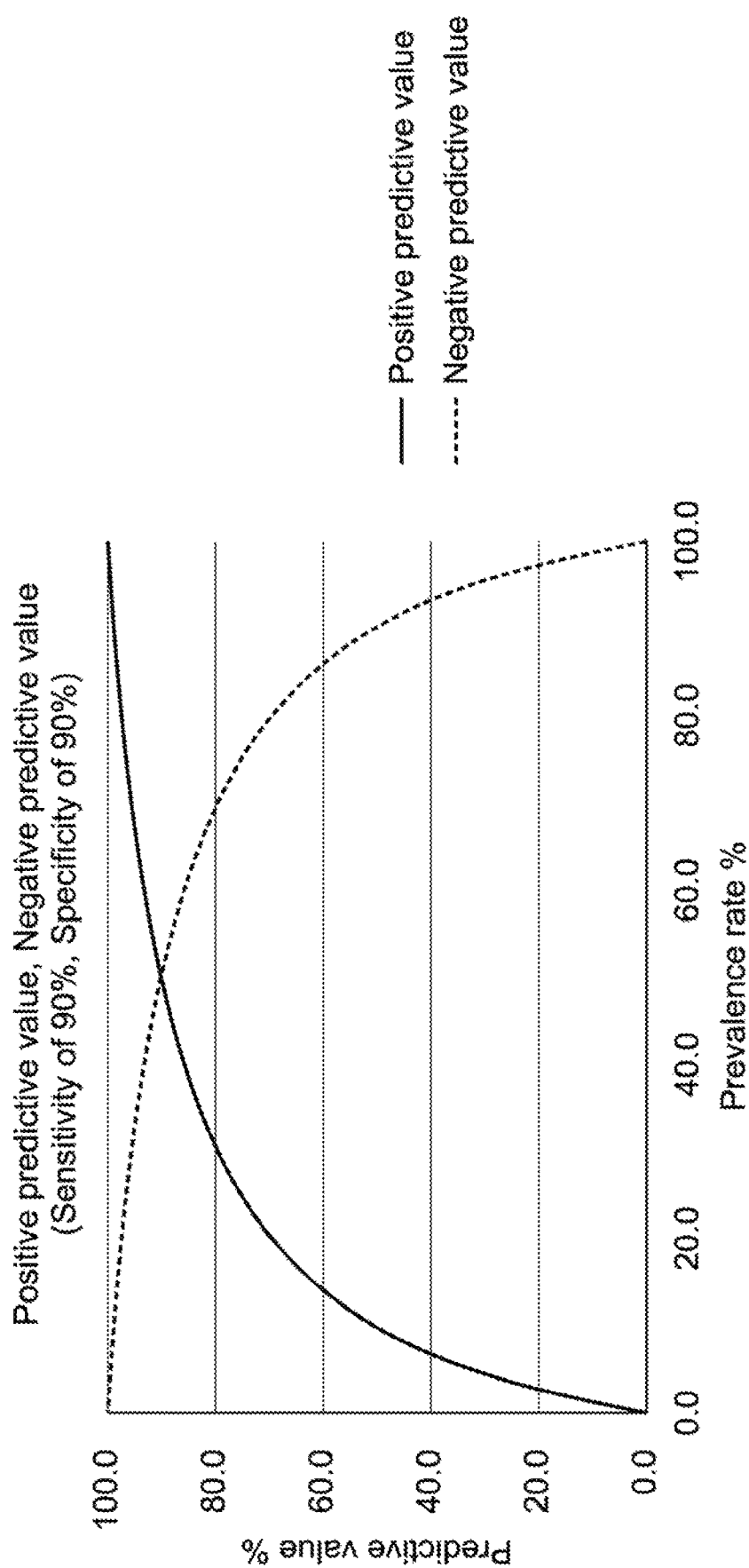
FIG. 2 is a graph showing a relationship between a positive predictive value and a negative predictive value, and a prevalence rate.

Hereinafter, embodiments of the present technology will be described with reference to the drawings.
[Regarding Background]

In test devices, test agents, and test kits (hereinafter, correctively referred to as test device) used in clinical practice, the degree of accuracy (=sensitivity) and the degree of accuracy (=specificity) are defined. With the degree of accuracy (=sensitivity), the test device can correctly determine an affected patient to be positive. With the degree of accuracy (=specificity), the test device can correctly determine an unaffected person to be negative. Those degrees of accuracy can be specified at the time the test device is manufactured. Until now, a final determination of a doctor on a test result has been made with reference to those indices in clinical tests.

In contrast to this, for the positive or negative result shown by the test device, there are indices of a positive predictive value and a negative predictive value that serve as indices representing a probability on whether a patient is actually affected with a disease or not.

The positive predictive value and the negative predictive value are very important indices, which represent a probability of a test result, for a doctor who uses the test device in clinical practice to determine a diagnosis of a disease. The reason why it is important will be described later. The positive predictive value and the negative predictive value can be calculated from the sensitivity and the specificity of the test device, and a prevalence rate. Conversely, in the case where the prevalence rate varies from hour to hour in infectious diseases and the like, the values of those indices also vary from hour to hour.

In the present technology, the prevalence rate, which varies from hour to hour, is adequately handled to assist a doctor to determine a more definite diagnosis using a test terminal in pandemic of an infectious disease, for example. This is one object to develop this test system.

In other words, examples in which information related to infection is provided by public institutions are already found, but it has been impossible to immediately provide detailed information to correspond to each test device or each patient. Immediately providing detailed information in such a manner is also one object to develop this test system.
[Regarding Prevalence Rate]

Here, the prevalence rate and indices related to the prevalence rate will be described simply. FIG. 1 shows a state where a clinical test of a certain disease is performed by a certain test method. Here, the number of persons who apply to a case (true positive) is "a", in which a positive result is obtained by a test device and a doctor makes a final determination for a certainty that the patient is affected with a disease. Further, the number of persons who apply to a case (false positive) is "c", in which a positive result is obtained by the test device but the doctor makes a final determination that the patient is not affected with the disease.

Furthermore, the number of persons who apply to a case (false negative) is "b", in which a negative result is obtained by the test device but the doctor makes a final determination that the patient is affected with the disease. Moreover, the number of persons who apply to a case (true negative) is "d", in which a negative result is obtained by the test device and the doctor makes a final determination that the patient is not affected with the disease.

From the definition of the figure, it is found that the prevalence rate is obtained by an expression $(a+b)/(a+b+c+d)$. Further, the definitions of indices related to the prevalence rate (positive, negative, positive rate, negative rate, positive predictive value, negative predictive value, number of diseases, number of non-diseases, total number, sensitivity, specificity, and accuracy) are as shown in the figure. It should be noted that in the case where there are a plurality of diseases or test methods, a table like this figure can be created for each combination of the diseases and the test methods.

Hereinbefore, the prevalence rate and the indices related to the prevalence rate have been described.
[Relationship Between Prevalence Rate, and Positive Predictive Value and Negative Predictive Value]

Next, a relationship between the prevalence rate, and the positive predictive value and the negative predictive value will be described.

First, according to Bayes' theorem, a probability (odds) that a patient is subjected to a certain test and determined to be actually affected with a disease is represented as the following mathematical expression (1), using pretest odds in which a positive result is obtained in a test before the test is performed, and a likelihood ratio.

$$\text{posttest odds} = \text{pretest odds} \times \text{likelihood ratio} \quad (1)$$

Further, odds ($\Omega$) are represented by the following mathematical expression (2) using a probability (p).

$$\Omega = p/(1-p) \quad (2)$$

It should be noted that from the mathematical expression (2), the probability (p) is represented by the following mathematical expression (3) using the odds ($\Omega$).

$$p = \Omega/(1+\Omega) \quad (3)$$

Further, posttest positive odds (that will be described later) are represented by the following mathematical expression (4) using the pretest odds and a positive likelihood ratio (that will be described later).

$$\text{posttest positive odds} = \text{pretest odds} \times \text{positive likelihood ratio} \quad (4)$$

Furthermore, posttest negative odds (that will be described later) are represented by the following mathematical expression (5) using the pretest odds and a negative likelihood ratio (that will be described later).

$$\text{posttest negative odds} = \text{pretest odds} \times \text{negative likelihood ratio} \quad (5)$$

Here, the definition expressions of relationships among other indices are also represented by the following mathematical expressions (6) to (11).

$$\text{prevalence rate} = \frac{\text{number of diseases}}{\text{total number}} \quad (6)$$

$$\text{pretest odds} = \frac{\text{prevalence rate}}{(1 - \text{prevalence rate})} \quad (7)$$

$$\text{posttest positive odds} = \frac{\text{positive predictive value}}{(1 - \text{positive predictive value})} \quad (8)$$

$$\text{posttest negative odds} = \frac{\text{negative predictive value}}{(1 - \text{positive predictive value})} \quad (9)$$

$$\text{positive likelihood ratio} = \frac{\text{sensitivity}}{(1 - \text{specificity})} = \frac{\left(\frac{\text{number of true positive}}{\text{number of diseases}}\right)}{\left(\frac{\text{number of false positive}}{\text{number of non-diseases}}\right)} \quad (10)$$

$$\text{negative likelihood ratio} = \frac{(1 - \text{sensitivity})}{\text{specificity}} = \frac{\left(\frac{\text{number of false negative}}{\text{number of diseases}}\right)}{\left(\frac{\text{number of true negative}}{\text{number of non-diseases}}\right)} \quad (11)$$

By the above mathematical expressions, the positive predictive value and the negative predictive value are represented by the following mathematical expressions (12) and (13) using the sensitivity, the specificity, and the prevalence rate.

$$\text{positive predictive value} = \text{sensitivity} \times \text{prevalence rate}/(\text{sensitivity} \times \text{prevalence rate} + (1 - \text{prevalence rate})(1 - \text{specificity})) \quad (12)$$

$$\text{negative predictive value} = \text{specificity} \times (1 - \text{prevalence rate})/(\text{specificity} \times (1 - \text{prevalence rate}) + \text{prevalence rate} \times (1 - \text{sensitivity})) \quad (13)$$

It should be noted that the mathematical expressions described above may be represented using the probability (p) or using the odds ($\Omega$), and information to be obtained are synonymous.

Hereinbefore, the fact that each of the positive predictive value and the negative predictive value can be represented as a function of the prevalence rate has been described.

Next, the relationship between the positive predictive value and the negative predictive value, and the prevalence rate will be described in more details. FIG. 2 is a graph showing a relationship between the positive predictive value and the negative predictive value, and the prevalence rate. It should be noted that in a test device to be used in this test, a sensitivity is 90%, and a specificity is 90%.

From the graph, for example, when the prevalence rate is 50%, that is, when the number of patients who are actually affected with a disease is approximately half the number of patients who are subjected to diagnoses, the positive predictive value and the negative predictive value are each approximately 90%, and it is found that a test result can be trusted.

However, for example, when the prevalence rate is approximately 5%, that is, when 100 persons are subjected to diagnoses and there are approximately 5 persons affected with a disease, the positive predictive value is approximately 30%, and it is found that a test result is difficult to trust.

Though not shown in this graph, for example, even in the case of using a test device having a sensitivity of 99% in order to increase the degree of accuracy of diagnosis, if the prevalence rate is extremely low, the positive predictive value falls below 50% and the reliability of the test result is reduced.

As described above, the prevalence rate is very important index for a doctor who makes a diagnosis of a disease based on clinical test results.

Hereinbefore, the relationship between the prevalence rate, and the positive predictive value and the negative predictive value has been described.

[Regarding Presentation of Treatment Plan Based on Positive Predictive Value and Negative Predictive Value]

Next, presentation of a treatment plan based on the positive predictive value and the negative predictive value will be described. Here, description will be given on a configuration to present a test plan and a treatment plan to be adopted next after a test based on the calculated positive predictive value and negative predictive value in the test terminal described above.

(Regarding Important Index in MRSA Infection)

Here, infection of MRSA (Methicillin-resistant *Staphylococcus aureus*) will be exemplified.

In order to prevent nosocomial infection, it is necessary to individually manage MRSA-infected patients. In the individual management, expense for infection prevention measures such as expense for a private room, and burdens of healthcare professionals, such as hand-washing and wearing of aprons, are required.

In order to reduce those burdens as much as possible, it is important to make a correct diagnosis on whether such a patient is really affected with MRSA or not. Examples of the test method include a genetic test, immunoassay, and a cultivation test. If the presence or absence of infection of MRSA is tested by those tests and a MRSA-uninfected person can be correctly diagnosed to be MRSA negative, the number of affected persons to be individually managed can be reduced, and the expense for infection prevention measures can be reduced. From this viewpoint, the negative predictive value is important regarding MRSA infection.

(Regarding Example of Plan Presented in MRSA Infection)

Next, a specific example will be given regarding a plan to be adopted depending on the levels of the sensitivity, the specificity, the prevalence rate, and the negative predictive value.

For example, when a test method in which the sensitivity is 85% and the specificity is 90% is used, if the prevalence rate is 40% or less, the negative predictive value of this test is 90% or more. The test terminal thus presents a recommendation for implementation of the test.

If the prevalence rate is more than 40%, the negative predictive value of this test is less than 90%. The test terminal thus does not recommend this test, and presents a recommendation for implementation of another test method with a higher sensitivity or a recommendation for implementation of individual management of patients without performing a test.

Similarly, when a test method in which the sensitivity is 90% and the specificity is 90% is used, if the prevalence rate is 50% or less, the negative predictive value is 90% or more. The implementation of the test is thus recommended. If the prevalence rate is above 50%, the negative predictive value is less than 90%. The test terminal thus does not recommend implementation of this test, and presents a recommendation for implementation of another test method with a higher sensitivity or a recommendation for implementation of individual management of patients.

Similarly, when a test method in which the sensitivity is 95% and the specificity is 90% is used and when the prevalence rate is 66.7% or less, the negative predictive value is 90% or more. The implementation of the test is thus recommended. If the prevalence rate is more than 66.7%, the negative predictive value is less than 90%. The test terminal thus does not recommend the test, and recommends another test method with a higher sensitivity or recommends individual management of patients.

(Regarding Recommendation of Test Method Based on Prevalence Rate)

Next, description will be given on what test method can be recommended to a doctor by the test terminal based on the prevalence rate.

As described above, there is a predetermined relationship among the sensitivity, the specificity, the prevalence rate, and the negative predictive value. In this regard, in the case where the negative predictive value is intended to be 90% or more when the prevalence rate is 30%, it is found that a test method with the sensitivity of 77% and the specificity of 90% or more only needs to be used.

Further, in the case where the negative predictive value is intended to be 90% or more when the prevalence rate is 40%, it is found that a test method with the sensitivity of 85% and the specificity of 90% or more only needs to be used.

Furthermore, in the case where the negative predictive value is intended to be 90% or more when the prevalence rate is 50%, it is found that a test method with the sensitivity of 90% and the specificity of 90% or more only needs to be used.

Moreover, in the case where the negative predictive value is intended to be 90% or more when the prevalence rate is 60%, it is found that a test method with the sensitivity of 93% and the specificity of 90% or more only needs to be used.

When this is applied to a specific case example, for example, the test terminal recommends a test method to be executed to a doctor as follows. Specifically, when the prevalence rate is 30%, use of an immunochromatographic test kit is recommended. The immunochromatographic test kit provides a low sensitivity but can suppress costs. When the prevalence rate is 50%, it is conceived that a genetic test kit that is expensive but provides a high sensitivity or a cultivation test that takes a long test time but provides a high sensitivity is recommended.

It should be noted that in the test system, a list of test methods that are feasible in healthcare facilities in which tests are performed may be held, and an optimum test method may be recommended to a doctor based on the sensitivity, the specificity, the prevalence rate, and the negative predictive value.

Hereinbefore, the configuration to present a test plan and a treatment plan to be adopted next after a test based on the calculated positive predictive value and negative predictive value in the test terminal has been described.

[Regarding Specific Example of Prevalence Rate]

Next, a specific example of the prevalence rate described above will be described. Here, an example will be described in which the prevalence rate changes depending on eras, regions, periods, ages, communities, and the like.

(Example in Which Prevalence Rate Changes Depending on Eras)

First, description will be given on a state where the prevalence rate of drug-resistant bacteria changes with the lapse of eras. Description here is based on information on a morbidity change in drug-resistant bacteria, which is created by CDC (Centers for Disease Control and Prevention) of the United States of America. It should be noted that the morbidity and the prevalence rate are similar indices. Here, the morbidity is replaced with the prevalence rate for description.

In the United States of America, the proportion of Methicillin-resistant *Staphylococcus aureus* (MRSA) to *Staphylococcus aureus* is approximately 5% in 1980, whereas the proportion changes to approximately 30% in 1990 and approximately 50% in 2000. Similarly, the proportion of Vancomycin-resistant *Enterococcus* (VRE) to enterococci or the proportion of Fluoroquinolone-resistant *Pseudomonas Aeruginosa* (FQRP) to pneumococci is 2% or less in 1990, whereas the proportion changes to 20% or more in 2000.

As described above, since the prevalence rate of drug-resistant bacteria changes with lapse of eras, in order to enhance the degree of accuracy of a diagnosis, it is important to grasp the latest prevalence rate when a test is performed.

(Example in Which Prevalence Rate Changes Depending on Regions (Countries))

Next, description will be given on a state where the prevalence rate of drug-resistant bacteria changes depending on regions (countries). Description here is based on materials of Euro Surveillance 2008 Nov. 20 Volume 13, Issue 47 by European Antimicrobial Resistance Surveillance System (EARSS). The materials show prevalence rates of drug-resistant bacteria on a country-by-country basis in Europe.

According to the materials of EARSS, the proportion of VRE to enterococci in 2007 is 30% or more in Ireland and Greece, 30 to 20% in the United Kingdom, 20 to 10% in Czech Republic, 10 to 5% in Italy, Germany, and Portugal, 5 to 1% in Spain, France, Switzerland, Austria, and other countries, and 1% or less in Norway, Sweden, Finland, Poland, and other countries.

As described above, since the prevalence rate also differs depending on regions and countries, in order to enhance the degree of accuracy of a diagnosis, it is important to grasp the latest prevalence rate of a region where a test is performed.

Example 1 of Prevalence Rate of Influenza Virus

Next, description will be given on a state where the prevalence rate of influenza virus fluctuates depending on periods and regions. Here, materials of Tokyo Metropolitan Institute of Public Health are used. The materials show the number of patients affected with influenza per sentinel on a period basis and on a yearly basis.

According to the materials, the prevalence rate of influenza virus tends to be low in June and July, whereas it tends to be high in February and March every year. However, in such a tendency, an epidemic start period differs yearly, and its prevalence rate also largely differs. Further, as in the epidemic of pandemic strains (H1pdm) in 2009, the prevalence rate is sometimes increased in October, November, and December in which the epidemic does not occur in usual years.

Further, though not shown in the figures here, also in Infectious Agents Surveillance Report (IASR, http://idsc-.nih.go.jp/iasr/influ.html) of National Institute of Infectious Diseases, the number of cases of infection of pathogens in sentinels and other healthcare facilities, health departments, and the like is reported as a report of infectious disease surveillance from prefectural and municipal public health institutes. According to the IASR, it is found that there is a difference in period and region of influenza epidemic. Additionally, there is a difference in period and region of influenza epidemic depending on types of influenza viruses.

As described above, the prevalence rate of the influenza virus largely differs depending on years, periods, and types of viruses. Therefore, in order to enhance the degree of accuracy of a diagnosis, a test system that can collect prevalence rate information very quickly and continuously when a test is performed is effective.

Example 2 of Prevalence Rate of Influenza Virus

Next, description will be given on a state where the prevalence rate of influenza virus fluctuates depending on ages of patients or communities to which patients belong. Here, materials of the Ministry of Health, Labour and Welfare and the Koriyama health department of Nara Prefecture are used. The materials show the number of estimated consultations of persons on an age group basis in the infectious disease surveillance of the Ministry of Health, Labour and Welfare.

According to the materials, the prevalence rate of influenza virus in the ages of 0 to 14, particularly in the ages of 5 to 9 tends to be higher than the other age groups. In other words, the prevalence rate largely changes depending on the age groups.

As a result, it is important to determine a test result using an optimum prevalence rate according to the age of a subject being tested.

Further, the prevalence rate also differs depending on communities to which patients belong. For example, the "Status of Pandemic Influenza in the season of 2012 to 2013", which is reported by the Koriyama health department of Nara Prefecture, provides a report example in which the prevalence rate of influenza virus in early elementary school years is high. For example, there is provided a report example in which the prevalence rate in the first year grade of a certain elementary school in the season of 2011 to 2012 is 30% or more.

On the other hand, according to the hospital admission surveillance and the infectious disease surveillance of the Ministry of Health, Labour and Welfare, the prevalence rate of influenza-like virus in the season of 2011 to 2012 in Japan is estimated as 16,480,000 persons. Assuming that the population of Japan is 128 million persons based on the result of the census in 2010, the prevalence rate of influenza virus is 12.9% at a maximum, which differs from the example of Nara Prefecture. In other words, this suggests that the prevalence rate of influenza virus differs depending on communities.

As a result, it is important to determine a test result using an optimum prevalence rate according to communities to which subjects being tested belong.

Hereinbefore, the specific example of the prevalence rate has been described.

[Regarding Configuration of Test System]

Figure 3:
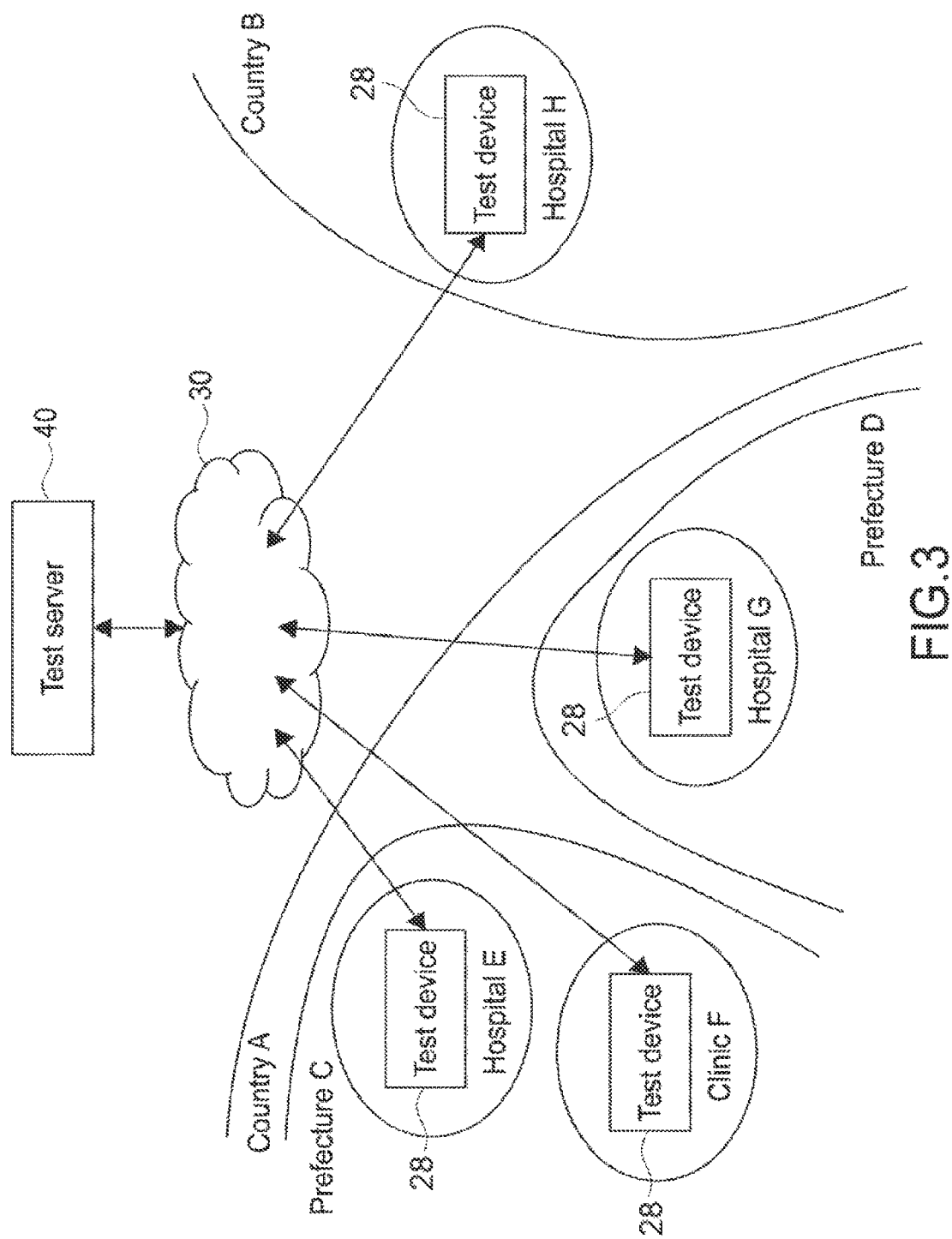
FIG. 3 is a diagram showing a configuration in which a test system 10 that adopts the present technology connects test terminals 20 with a test server 40 via a network.

Next, the overall configuration of a test system to which the present technology is applied will be described. In a test system using the present technology, a client server configuration is adopted. FIG. 3 is a diagram showing a configuration in which a test system 10 that adopts the present technology connects test terminals 20 with a test server 40 via a network. As shown in this figure, in the test system 10 that adopts the present technology, a plurality of test terminals 20 serving as clients are dispersedly disposed in countries, regions, and facilities and are connected to the test server 40 via the network 30.

(Reason Why Client Server Configuration is Adopted)

First, the reason why the test system 10 that adopts the present technology has to have a client server configuration will be described.

As described above, using the latest prevalence rate is one of points in the present technology. As found from the definition described above, regarding this prevalence rate, as the total number of tests becomes larger, the degree of accuracy of a calculated prevalence rate becomes higher.

Further, in order to increase the total number of tests, there are an approach to performing many tests in one test terminal and an approach to collecting test results from many test terminals. In the present technology, in order to achieve an approach to collecting test results from many test terminals, a client server configuration formed of the test server 40 and the plurality of test terminals 20 is adopted as a configuration of the test system 10.

Adopting this configuration allows the number of test terminals 20 serving as clients to be increased as much as possible. This can improve the degree of accuracy of the prevalence rate provided from the test server 40 to the test terminals 20.

(Regarding Configuration of Test Server 40)

Figure 4:
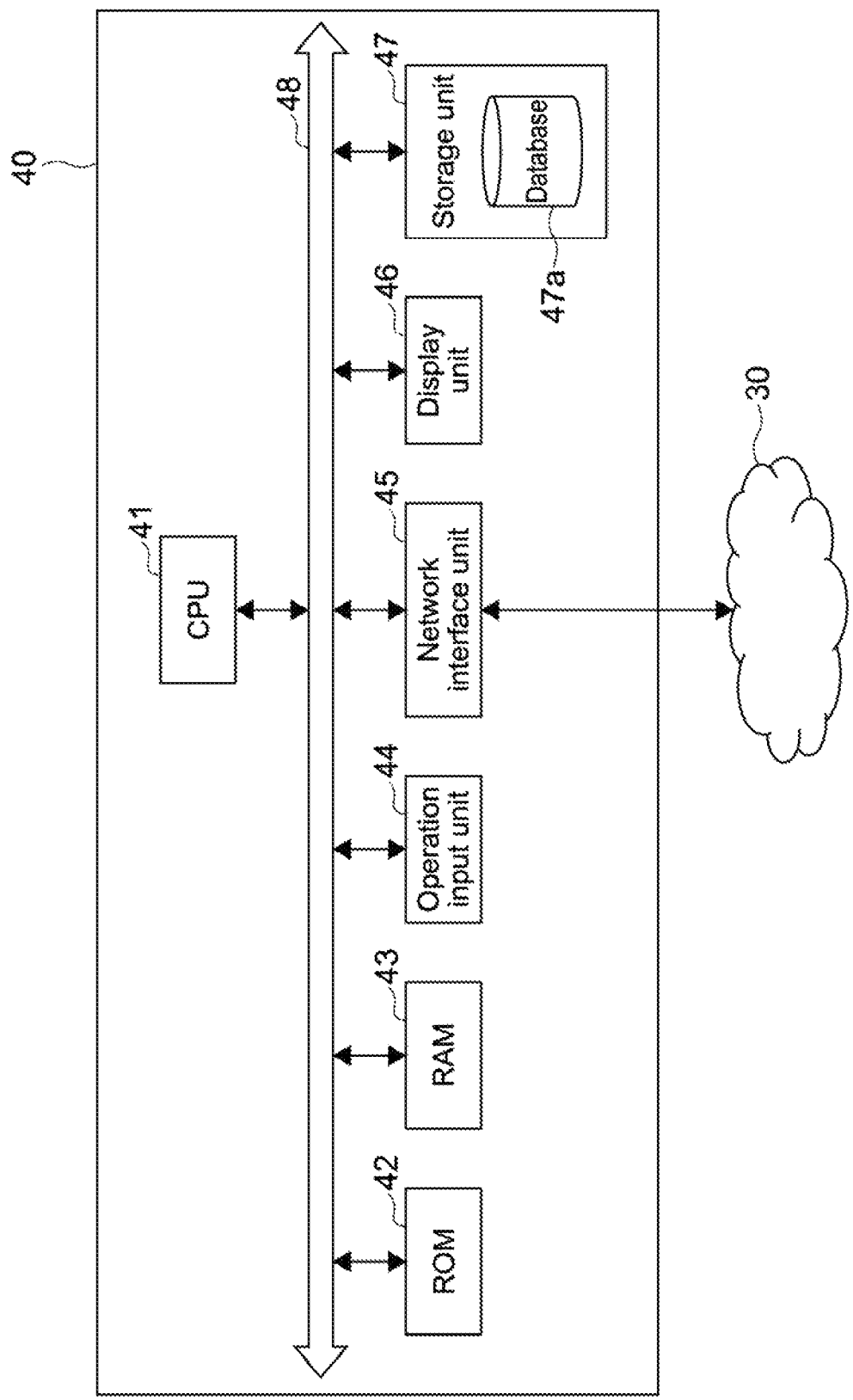
FIG. 4 is a block diagram of a case where the test server 40 is configured by a general computer.

Next, a hardware configuration of the test server 40 will be described. The test server 40 may be configured by dedicated hardware or software or may be configured by a general computer. FIG. 4 is a block diagram of a case where the test server 40 is configured by a general computer.

As shown in the figure, the test server 40 includes a CPU (Central Processing Unit, control unit, first control unit) 41, a ROM (Read Only Memory) 42, a RAM (Random Access Memory) 43, an operation input unit 44, a network interface unit (communication unit, first communication unit) 45, a display unit 46, and a storage unit 47, and those blocks are connected to one another via a bus 48.

The ROM 42 fixedly stores a plurality of programs and data such as firmware to execute various types of processing. The RAM 43 is used as a work area of the CPU 41 and temporarily holds an OS (Operating System), various applications being executed, and various types of data being processed.

The storage unit 47 is, for example, an HDD (Hard Disk Drive), a flash memory, or another non-volatile memory such as a solid-state memory. In the storage unit 47, a database 47a that will be described later is stored in addition to the OS, the various applications, and the various types of data.

The network interface unit 45 is connected to the network 30 for exchanging information with the test terminals 20, and collects information from the test terminals 20 or provides processed information to the test terminals 20.

The CPU 41 develops a program corresponding to a command provided from the operation input unit 44, in a plurality of programs stored in the ROM 42 and the storage unit 47, to the RAM 43 and appropriately controls the display unit 46 and the storage unit 47 according to the developed program.

Further, the CPU 41 updates the database 47a based on information collected from the test terminals 20 via the network 30 and the network interface unit 45. The CPU 41 then extracts necessary information from the database 47a based on a condition specified by a demand of the information received from the test terminals 20, counts and returns the information to the test terminals 20.

The operation input unit 44 is, for example, a pointing device such as a mouse, a keyboard, a touch panel, or another operating device.

The display unit 46 is, for example, a liquid crystal display, an EL (Electro-Luminescence) display, a plasma display, or a CRT (Cathode Ray Tube) display. The display unit 46 may be incorporated in the test server 40 or may be externally connected.

Hereinbefore, the configuration of the test server 40 has been described.

(Regarding Database 47a)

Next, a configuration example of records stored in the database 47a will be described. FIG. 5 is a diagram showing an example of fields (items) in each record that configures the database 47a. It should be noted that those items are referred to as test information items.

In the example of this diagram, the items of Instrument ID, Patient ID, Sample ID, Date (date of test), Address (address, administrative district), Country, Gender, Age, Assay result (test result), Diagnosis (diagnosis of doctor) are arranged from the left.

Those items are examples. More items may be provided, or those items may be narrowed down to less items depending on the types of information to be collected, extracted, and counted by the test server 40. In the case where the number of items is increased, for example, Disease ID, Test method ID, and the like may be added. The addition of those Disease ID and Test method ID allows this test system to correspond to a plurality of disease or a plurality of test methods. It should be noted that a method of using those items is described later.

(Regarding Configuration of Test Terminal 20)

Figure 6:
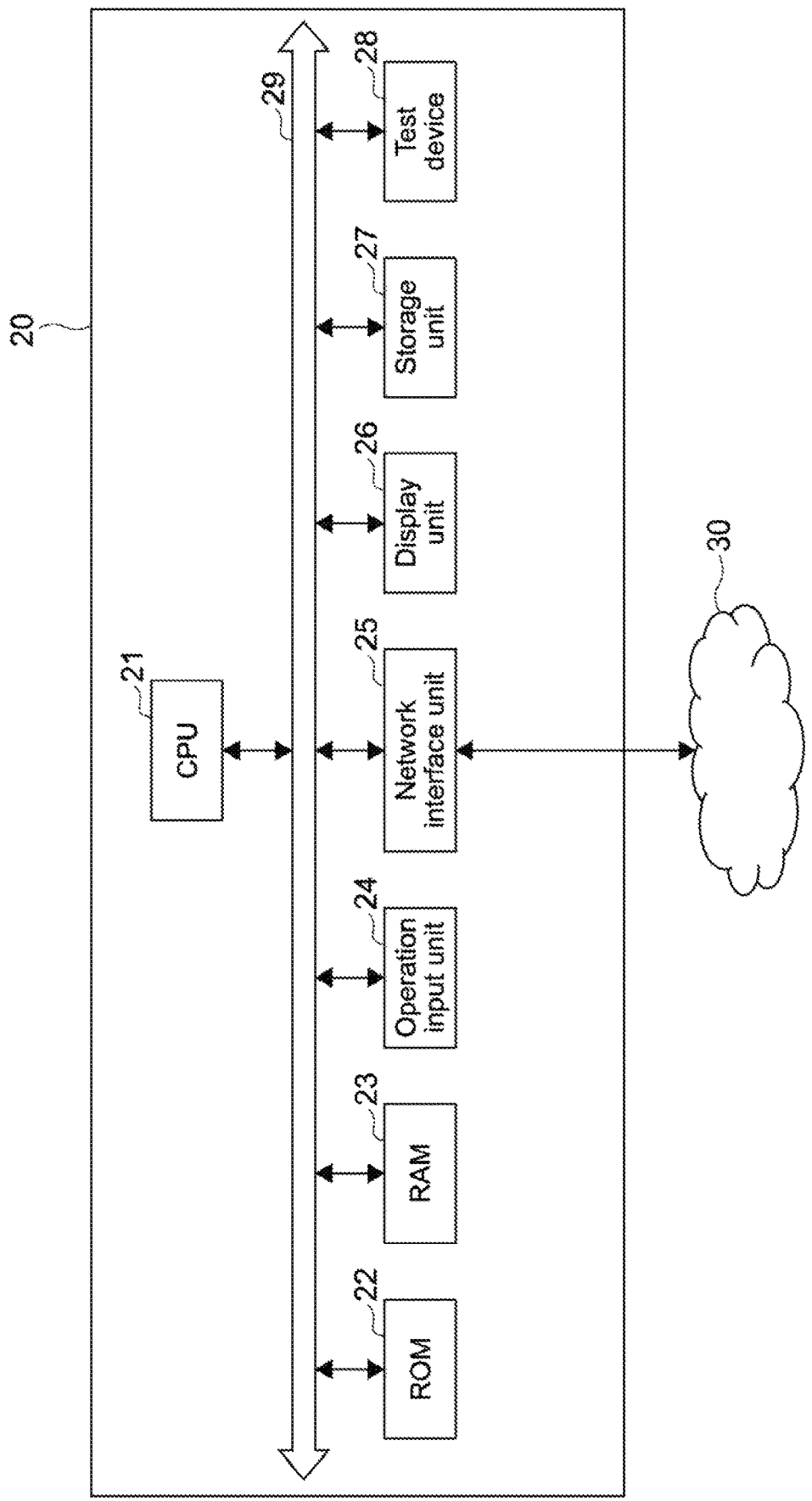
FIG. 6 is a block diagram of a case where the test terminal 20 is configured by a test device and a general computer.

Next, a hardware configuration of the test terminal 20 will be described. The test terminal 20 may be configured by dedicated hardware or software or may be configured by a test device and a general computer. FIG. 6 is a block diagram of a case where the test terminal 20 is configured by a test device and a general computer.

As shown in the figure, the test terminal (communication terminal) 20 includes a CPU (control unit, second control unit) 21, a ROM 22, a RAM 23, an operation input unit (input unit) 24, a network interface unit (communication unit, second communication unit) 25, a display unit 26, a storage unit 27, and a test device 28, and those blocks are connected to one another via a bus 29. It should be noted that description of constituent elements having the same functions as those of the test server 40 will be omitted.

The network interface unit 25 is connected to the network 30 for exchanging information with the test server 40, and transmits information to the test server 40 or receives information processed in the test server 40.

The CPU 21 presents information, which is received from the test server 40 via the network 30 and the network interface unit 25, to a user or a doctor via the display unit 26, or performs various types of processing based on the received information. The various types of processing will be described later. Further, the CPU 21 transmits a test result in the test device 28 or a final diagnosis of a doctor who made a diagnosis of a disease to the test server 40 via the network 30 and the network interface unit 25.

The test device 28 is a device with which a disease is actually tested. A test result is read by the CPU 41, and then presented to a doctor who performed the test via the display unit 26 or transmitted to the test server 40 via the network 30. It should be noted that in the case where a test kit is used as the test device, the test terminal 20 may automatically read a test result, or a test result may be input to the test terminal 20 manually.

Hereinbefore, the configuration of the test terminal 20 has been described.

[Regarding Processing Flow of Test System 10]

Next, a processing flow performed in the test system 10 will be described. First, the overall flow will be described. Next, details of individual processing will be described. Lastly, a processing flow will be described as an application example or a modified example.

(Overall Processing Flow)

Figure 7:
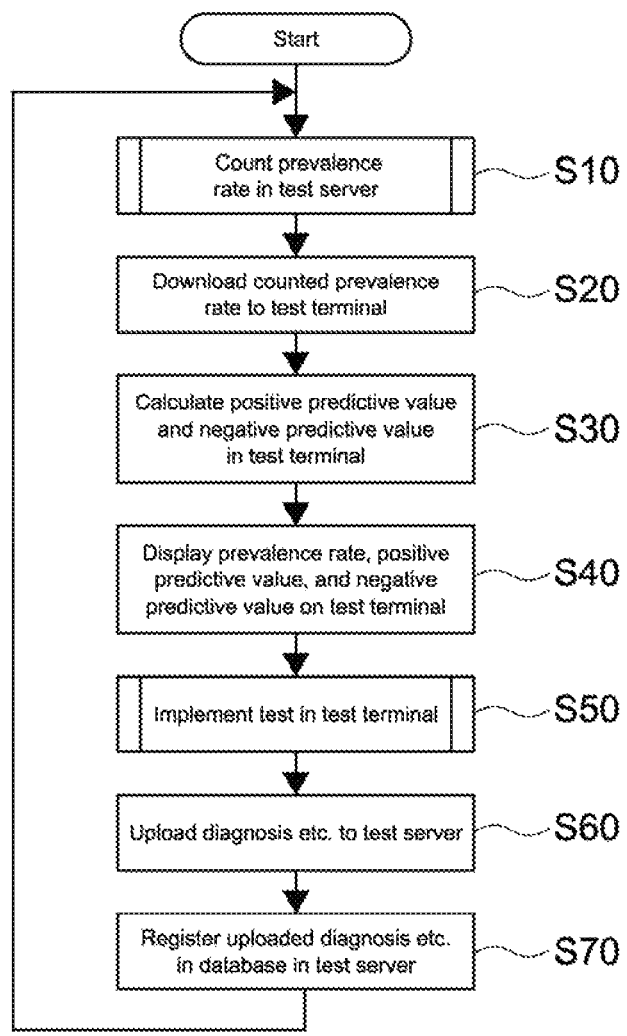
FIG. 7 is a flowchart for describing the overall processing flow in the test system 10.

First, an overall processing flow in the test system 10 will be described. FIG. 7 is a flowchart for describing the overall processing flow in the test system 10.

First, the CPU 41 of the test server 40 counts and calculates a prevalence rate for one disease and one test method using the database 47a in the test server 40 (Step S10). It should be noted that details of this count and calculation processing are described later. It should be noted that the count and calculation processing may be started on a certain-time-period basis (for example, every hour or every day) or may be started using, as a trigger, a request (demand) from a test terminal 20 with which a doctor will implement a test.

Next, in the test terminal 20 with which a test will be implemented, the CPU 21 of the test terminal 20 downloads the prevalence rate calculated in the test server 40 (Step S20). It should be noted that downloading may be performed by pull communication from the test terminal 20 or by push communication from the test server 40.

Next, in the test terminal 20 that downloads the prevalence rate, the CPU 21 calculates a positive predictive value and a negative predictive value according to the mathematical expressions (12) and (13) described above (Step S30). It should be noted that the mathematical expressions are shown below again. Further, it is assumed that the values of the sensitivity and the specificity are preliminarily held by the test terminal 20.

$$\text{positive predictive value} = \text{sensitivity} \times \text{prevalence rate} / (\text{sensitivity} \times \text{prevalence rate} + (1 - \text{prevalence rate})(1 - \text{specificity})) \quad (12)$$

$$\text{negative predictive value} = \text{specificity} \times (1 - \text{prevalence rate}) / (\text{specificity} \times (1 - \text{prevalence rate}) + \text{prevalence rate} \times (1 - \text{sensitivity})) \quad (13)$$

It should be noted that the positive predictive value and the negative predictive value may be directly obtained from expressions a/(a+c) and d/(b+d), respectively, without using the prevalence rate.

Next, in the test terminal 20 that downloads the prevalence rate, the CPU 21 presents the prevalence rate, the positive predictive value, and the negative predictive value to a user or a doctor via the display unit 26 (Step S40).

Next, in the test device 28 of the test terminal 20 that downloads the prevalence rate, a test is implemented according to an instruction of the user (Step S50). Details of the processing of the test will be described later.

Next, in the test terminal 20 that downloads the prevalence rate, the CPU 21 uploads a diagnosis etc. (test information), which is input to the test terminal 20, to the test server 40 (Step S60). It should be noted that the test information uploaded here may be the same as the items that configure records of the database 47a described above. Further, uploading may be directly performed from the test terminal 20 or may be performed via a laboratory information system (LIS) or a smartphone. Details of an uploading method will be described later.

Next, in the test server 40, the CPU 41 registers the uploaded test information such as a diagnosis in the database 47a (Step S70).

After the registration in the database 47a in Step S70, the processing returns to Step S10 and the processing described above is repeated.

Hereinbefore, the overall processing flow in the test system 10 has been described.

(Regarding Count and Calculation Processing of Prevalence Rate)

Figure 8:
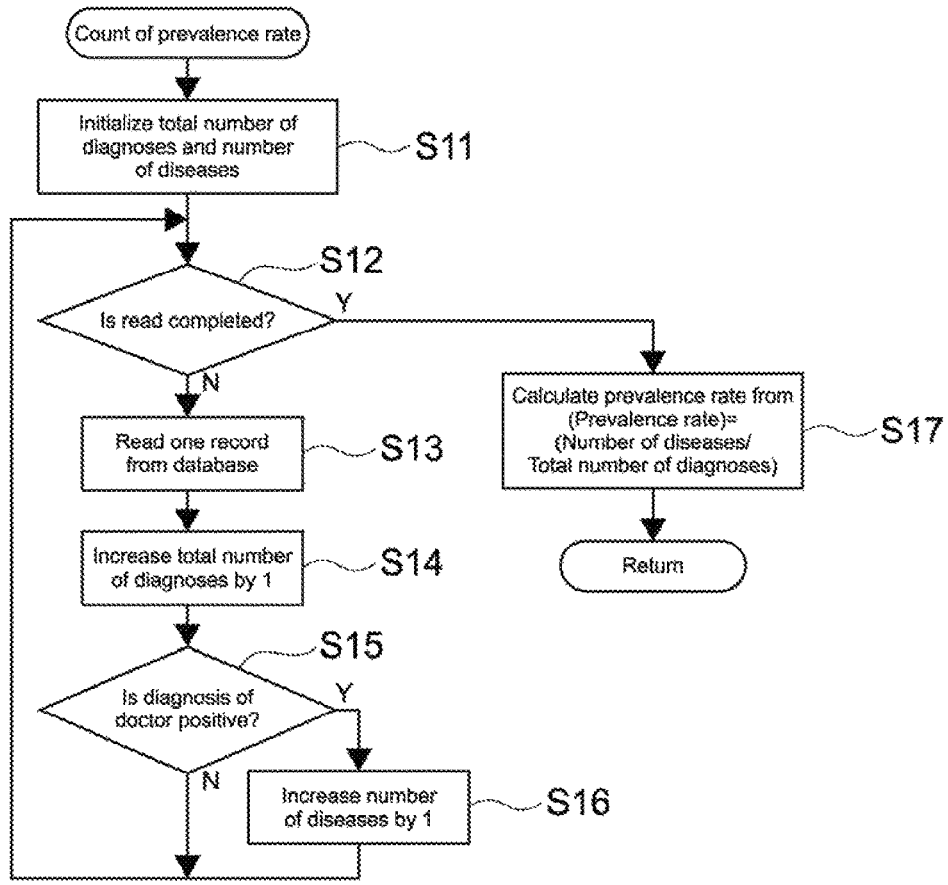
FIG. 8 is a flowchart for describing the details of processing to count and calculate a prevalence rate.

Next, details of the processing to count and calculate the prevalence rate described above will be described. FIG. 8 is a flowchart for describing the details of the processing to count and calculate the prevalence rate.

First, the CPU 41 of the test server 40 clears the total number of diagnoses and the number of diseases to zero for initialization. The total number of diagnoses and the number of diseases are variables used for count up at the time of count (Step S11).

Next, the CPU 41 determines whether all records of the database 47a are read or not (Step S12). It should be noted that whether all records are read or not is determined in the case where the database 47a is constituted by records related to one disease and one test method. In the case where the records related to a plurality of diseases and a plurality of test methods are included in the database 47a, whether all records related to diseases or test methods to be counted are read or not may be determined.

At this moment, since all the records of the database 47a are not yet read (N of Step S12), the CPU 41 then reads one record from the database 47a (Step S13).

Next, the CPU 41 counts up the total number of diagnoses by 1 (Step S14).

Next, the CPU 41 determines whether "Diagnosis" of the doctor, which is one field of the read record, is positive or not (Step S15).

Only in the case where the result is positive (Y of Step S15), the CPU 41 counts up the number of diseases by 1 (Step S16).

In the case where the result is negative in Step S15 (N of Step S15) of after the number of diseases is counted up in Step S16, the CPU 41 returns to the processing of Step S12 and continues the processing.

In Step S12, in the case where all records of the database 47a are read (Y of Step S12), the CPU 41 then calculates a prevalence rate from the total number of diagnoses and the number of diseases according to the mathematical expression (6) (Step S17). It should be noted that the mathematical expression (6) is as follows.

$$\text{prevalence rate} = \text{number of diseases/total number} \quad (6)$$

Hereinbefore, the details of the processing to count and calculate the prevalence rate have been described. It should be noted that in the above description, all the records in the database 47a are to be processed, but the present technology is not limited thereto. For example, the following configuration may be provided: an item of "data registration date and time" is provided to a record, and only a record registered within a certain period of time in the past is processed.

Further, in the above description, the records in the database 47a are counted so as to obtain the prevalence rate, but the present technology is not limited thereto. The following configuration may be provided: a value of the prevalence rate is acquired from outside the test system 10. An acquisition method may be a method passing through the network 30 or may be a method of extracting a numerical value of the prevalence rate from a research paper and the like and manually inputting the numerical value to the test server 40. When a numerical value from a research paper and the like is manually input to the test server 40, it is desirable to have a standard to simplify the input.

(Regarding Implementation of Test)

Figure 9:
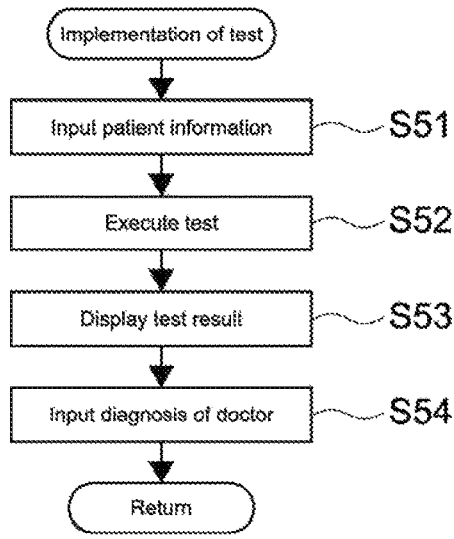
FIG. 9 is a flowchart for describing the details of the implementation of a test.

Next, details of the implementation of the test described above will be described. FIG. 9 is a flowchart for describing the details of the implementation of a test.

First, the user inputs patient information via the operation input unit 24 or the like of the test terminal 20 (Step S51).

Next, according to an instruction of the user or the CPU 21 of the test terminal 20, a test is executed in the test device 28 (Step S52).

Next, the CPU 21 reads a test result in the test device 28 and presents the test result to the user or the doctor via the display unit 26 (Step S53).

Next, the doctor inputs a final diagnosis to the test terminal 20, based on the prevalence rate, the positive predictive value, the negative predictive value, and the test result that are displayed in the test terminal 20 (Step S54). When the diagnosis is input, the doctor can determine a final diagnosis with higher degree of accuracy by referring to the prevalence rate, the positive predictive value, and the negative predictive value.

Hereinbefore, the details of the implementation of a test have been described.

Modified Example 1 Calculation of Positive Predictive Value Etc. In Test Server 40

In the above description, the processing has been described in which the test terminal 20 has information of the test terminal's sensitivity and specificity, and downloads only the prevalence rate from the test server 40 to calculate the positive predictive value and the negative predictive value on the test terminal 20 side.

In contrast to this, in a modified example to be described here, the test server 40 holds information on the sensitivities and specificities of various types of test devices 28. It should be noted that for values of the sensitivity and the specificity used here, values that are specific to the test devices 28 and provided as performance of the test devices 28 by manufacturers of the test devices 28 can be used. Before demanding information such as the prevalence rate, the test terminal 20 notifies the test server 40 of the device ID and the like of the test terminal 20. The test server 40 calculates a positive predictive value and a negative predictive value in the test server 40 using the values of the sensitivity and the specificity, which are associated with the notified device ID. The test terminal 20 downloads the prevalence rate, the positive predictive value, and the negative predictive value from the test server 40 and presents them to the user.

Adopting this configuration allows the test terminal to omit the processing to calculate the positive predictive value and the negative predictive value. Further, the sensitivity and the specificity of each test terminal 20 can be arbitrarily adjusted on the test server 40 side.

Modified Example 2 Download and Presentation of More Information

In the above description, only the prevalence rate is downloaded or three of the prevalence rate, the positive predictive value, and the negative predictive value are downloaded from the test server 40 to the test terminals 20. In contrast to this, in a modified example to be described here, more information may be downloaded and presented to the user. Examples of the more information include the total number of diagnoses and the number of diseases. By presentation of such information to the user, the adequacy of the calculated positive predictive value and negative predictive value can be determined.

Modified Example 3 Improvement of Predictive Value by Adequate Sensitivity/Specificity In the above description, the sensitivity and the specificity are uniquely determined in the test device 28. In contrast to this, in a modified example to be described here, a configuration will be described in which the sensitivity and the specificity are changed based on the elapsed time from the development of a disease such as an infection disease.

For example, in the case of a respiratory tract infection disease, it is known that the number of pathogens in the nasal cavity or pharynx fluctuates with the elapsed time from the development of a disease. Along with the change in the number of pathogens, the sensitivity and the specificity of a test also fluctuate. As a result, based on the elapsed time from the development of a disease of a patient, the degree of accuracy of the positive predictive value and negative predictive value to be obtained can be improved using adequate values of the sensitivity and the specificity.

Figure 10:
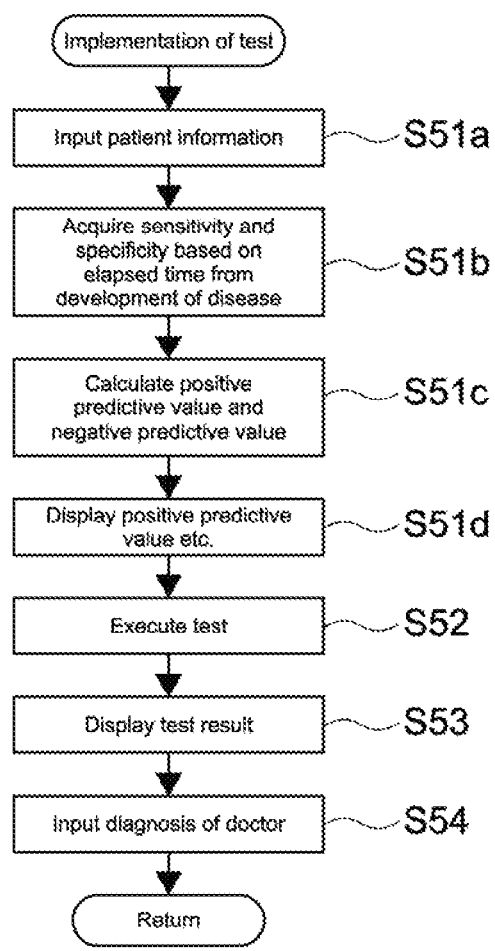
FIG. 10 is a flowchart for describing processing using a sensitivity and a specificity that are based on an elapsed time from the development of a disease, in processing to implement a test.

FIG. 10 is a flowchart for describing processing using a sensitivity and a specificity that are based on an elapsed time from the development of a disease, in the above-mentioned processing to implement a test.

First, the user inputs patient information to the test terminal 20 (Step S51a). When the patient information is input, an elapsed time from the development of a disease is also input.

Next, the CPU 21 of the test terminal 20 acquires a sensitivity and a specificity based on the input elapsed time from the development of a disease (Step S51b). It should be noted that a sensitivity and a specificity to be acquired may be preliminarily held in the test terminal 20 or may be downloaded from the test server 40 that holds the sensitivity and specificity.

It is desirable to have a standard for facilitating the acquisition of the sensitivity and the specificity. For example, it may be possible to display a bar code on the package of a diagnosis kit and scan the bar code, to capture a specific sensitivity and specificity into the test system 10.

Further, it may also be possible to establish a database on the sensitivity and the specificity of each test device 28 in the test system 10 and acquire, based on a medical-device identification number of the test device 28, the sensitivity and specificity of the test device 28, a sensitivity and specificity on an disease-development-time basis, a sensitivity and specificity on a patient's age basis, and the like.

Next, the CPU 21 calculates a positive predictive value and a negative predictive value using the acquired prevalence rate, sensitivity, and specificity (Step S51c).

Next, the CPU 21 presents the calculated positive predictive value and negative predictive value to the user (Step S51d). It should be noted that when the positive predictive value and the negative predictive value are presented to the user, the acquired prevalence rate, sensitivity, and specificity may also be presented together.

Processing of Step S51d and steps subsequent thereto are the same as those described above, and thus description thereof will be omitted.

Hereinbefore, the configuration has been described in which the sensitivity and the specificity are changed based on the elapsed time from the development of a disease such as an infection disease.

(Modified Example 4 Combination of Plurality of Tests (Integration of Test Results))

In the above description, the configuration in which one test is executed as a test of a disease has been described. In contrast to this, in a modified example to be described here, a configuration will be described in which various types of tests are executed and results of the tests are integrated, to output a final test result (which is not a final diagnosis). In the configuration of this modified example, various types of tests may be executed, and only in the case where results in all the tests are positive, a final test result may be considered to be positive. This allows the degree of accuracy of likelihood (sensitivity and specificity) to be improved, and also allows the degree of accuracy of a positive predictive value and a negative predictive value, which are finally calculated, to be improved.

Figure 11:
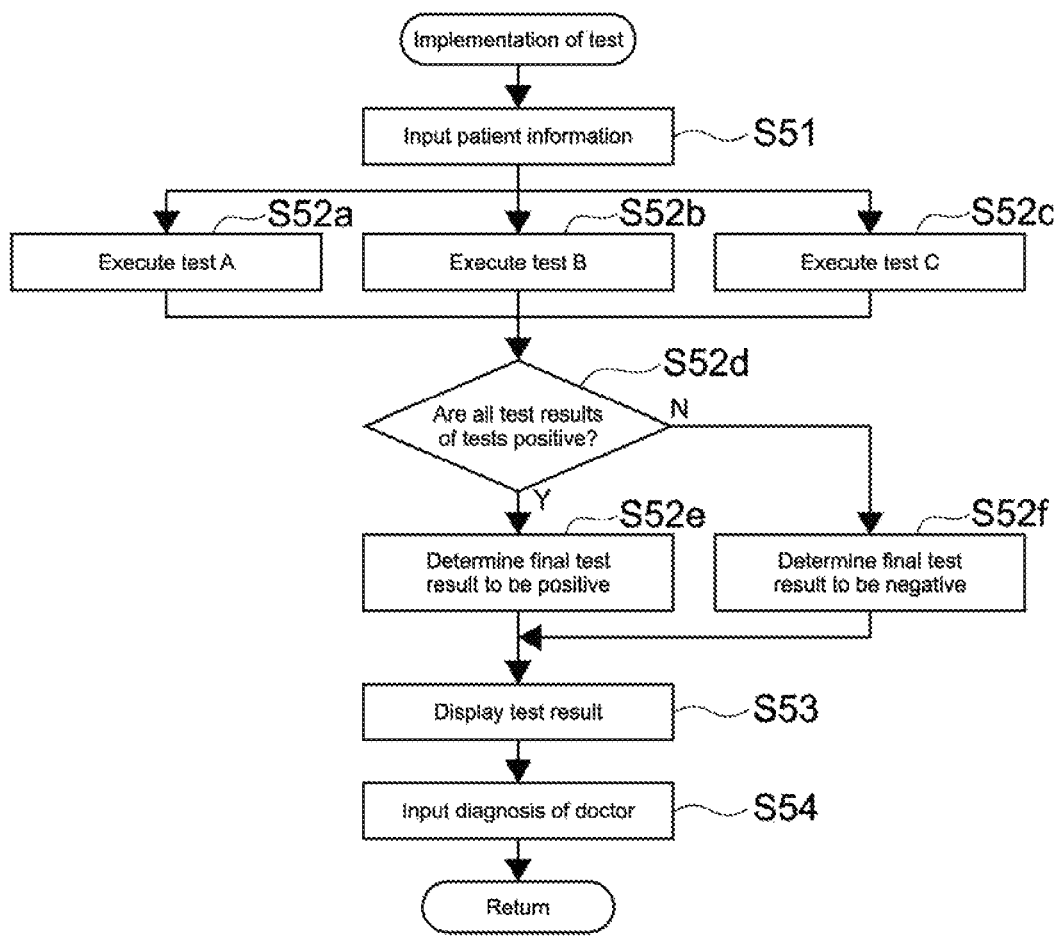
FIG. 11 is a flowchart for describing processing in which various tests are performed and results of the tests are comprehensively used in the processing to implement a test.

FIG. 11 is a flowchart for describing processing in which various tests are performed and results of the tests are comprehensively used in the above-mentioned processing to implement a test.

First, the user inputs patient information (Step S51). This step is the same as the step described above.

Next, the test terminal 20 executes various types of tests (in this example, three types of tests A, B, and C) (Step S52a, 52b, and 52c). The tests may be executed simultaneously and parallel or executed sequentially one by one. It should be noted that the determination of test results is performed after all test results are obtained.

Next, the CPU 21 of the test terminal 20 determines whether all the test results of the respective tests are positive or not (determines test results showing the presence of disease) (Step S52d).

In the case where all the results are positive (Y of Step S52d), the CPU 21 determines a final test result to be positive (Step S52e). Here, although a final test result is determined to be positive in the case where all the test results are positive, there may be a case where the CPU 21 determines a final test result to be positive when all the results are not necessarily positive, depending on conditions such as the sensitivity of each test.

In the case where any of the results is negative (N of Step S52d), the CPU 21 determines a final test result to be negative (determines test results showing the absence of disease) (Step S52f).

Processing of Step 53 and steps subsequent thereto are the same as those described above, and thus description thereof will be omitted. It should be noted that the following processing is performed using the "final test result" obtained here as the "test result" described above.

Hereinbefore, the configuration in which various types of tests are executed, results of the tests are integrated, and a final test result is output has been described.

Modified Example 5 Combination of Plurality of Tests (Stepwise Execution of Tests)

In the above modified example in which a plurality of tests are combined, the configuration in which after all the tests are performed, all test results are integrated for processing has been described. In contrast to this, in a modified example to be described here, a plurality of tests are executed one by one, and each time one test result is obtained, whether to continue a test or not is determined. In this modified example, stepwise execution of tests allows the degree of accuracy of a final diagnosis based on the prevalence rate to be improved.

In the configuration of this modified example, for example, in the case where tests A, B, and C are sequentially performed and when results of the respective tests are determined to be positive, the odds that a patient is determined to be truly positive are increased. According to posttest odds (posttest positive odds and posttest negative odds) of the respective tests, a trade-off between costs of subsequent tests and side effects that may be caused can be considered. Depending on circumstances, it is also possible to make a choice to perform no subsequent tests, determine the patient to be positive, and advance the treatment of the patient.

Figure 12:
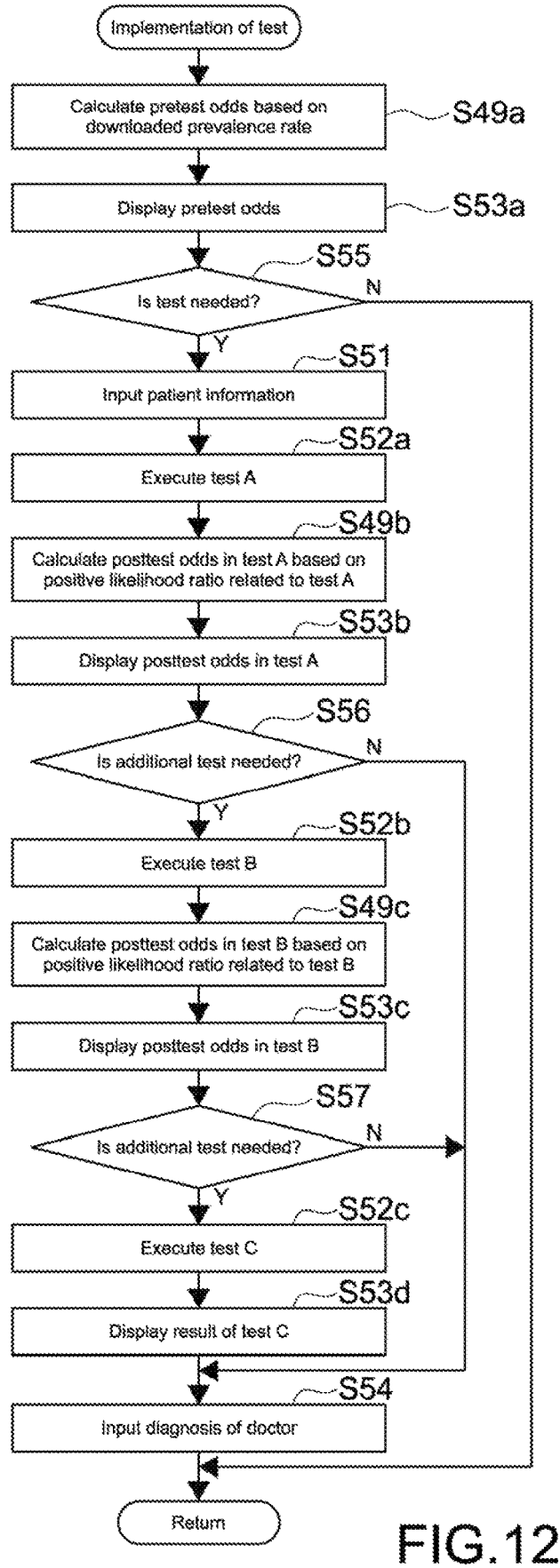
FIG. 12 is a flowchart for describing processing in which a plurality of tests are executed one by one and each time one test result is obtained, whether the test is continued or not is determined, in the processing to implement a test.

FIG. 12 is a flowchart for describing processing in which a plurality of tests are executed one by one and each time one test result is obtained, whether the test is continued or not is determined, in the above-mentioned processing to implement a test. Here, a configuration in which tests A, B, and C are sequentially performed as a plurality of tests is provided.

First, the CPU 21 of the test terminal 20 calculates pretest odds based on the prevalence rate downloaded from the test server 40, using the mathematical expression (7) (Step S49a).

Next, the CPU 21 presents the calculated pretest odds to the user or the doctor via the display unit 26 (Step S53a).

Next, the doctor determines whether the test A is needed to be executed or not (Step S55).

In the case where the execution is determined to be unnecessary (N of Step S55), no tests are performed.

In the case where the execution of the test A is determined to be necessary (Y of Step S55), the operation input unit 24 then receives an input of patient information from the user (Step S51).

Next, the test device 28 of the test terminal 20 executes the test A (Step S52a).

Next, the CPU 21 calculates posttest positive odds in the test A based on a result of the test A and on pretest odds and a positive likelihood ratio related to the test A, using the mathematical expression (4) (Step S49b). It should be noted that the positive likelihood ratio is used here, but the present technology is not limited thereto. A configuration in which at least one of the positive likelihood ratio and the negative likelihood ratio is used may be adopted.

Next, the CPU 21 presents the posttest positive odds to the user (Step S53b).

Next, the doctor determines whether an additional test is needed or not by referring to the presented posttest positive odds (Step S56).

In the case where an additional test is determined to be unnecessary (N of Step S56), the test B and the test C are not performed. The processing proceeds to the input of the diagnosis of the doctor (Step S54).

In the case where an additional test is determined to be necessary (Y of Step S56), the CPU 21 then causes the test device 28 to execute the test B (Step S52b).

Next, the CPU 21 calculates posttest positive odds in the test B, as in Step S49b, based on the test result of the test A, a test result of the test B, and pretest odds and a positive likelihood ratio related to the test B (Step S49c).

Next, the CPU 21 presents the calculated posttest positive odds to the user or the doctor (Step S53c).

Next, the doctor determines whether a further additional test is needed or not (Step S57).

In the case where a further additional test is determined to be unnecessary (N of Step S57), the test C is not performed. The processing proceeds to the input of the diagnosis of the doctor (Step S54).

In the case where a further additional test is determined to be necessary (Y of Step S57), the CPU 21 then causes the test device 28 to execute the test C (Step S52c).

Next, the CPU 21 presents a test result of the test C to the user (Step S53d).

Next, the doctor inputs a final diagnosis to the test terminal 20 by referring to the test result (Step S54).

Hereinbefore, the processing to execute a plurality of tests one by one and determine whether to continue a test or not each time one test result is obtained has been described.

Modified Example 6 Narrowing-Down of Target Data Based on Attribute of Test Terminal In the above description, the prevalence rate is counted and calculated for all records stored in the database 47a, that is, all the test results. In contrast to this, in a modified example to be described here, a configuration will be described in which test results to be the basis for counting and calculating the prevalence rate are narrowed down based on an attribute of the test terminal 20 (terminal attribute information).

In an example described here, test results used to calculate the prevalence rate are narrowed down to only results of tests performed in an administrative district (for example, Tokyo) to which a test terminal 20 that demands a prevalence rate belongs, or to only test results acquired within the range of a physical distance (for example, 50 km) from the test terminal 20. In other words, the narrowing-down is performed based on the attribute of the test terminal 20. It should be noted that the narrowing-down used here refers to using only test results matched with a certain condition to count the prevalence rate.

As described above, various types of narrowing-down are performed when the prevalence rate is calculated. This allows more adequate information to be provided to the individual test terminals 20.

Figure 13:
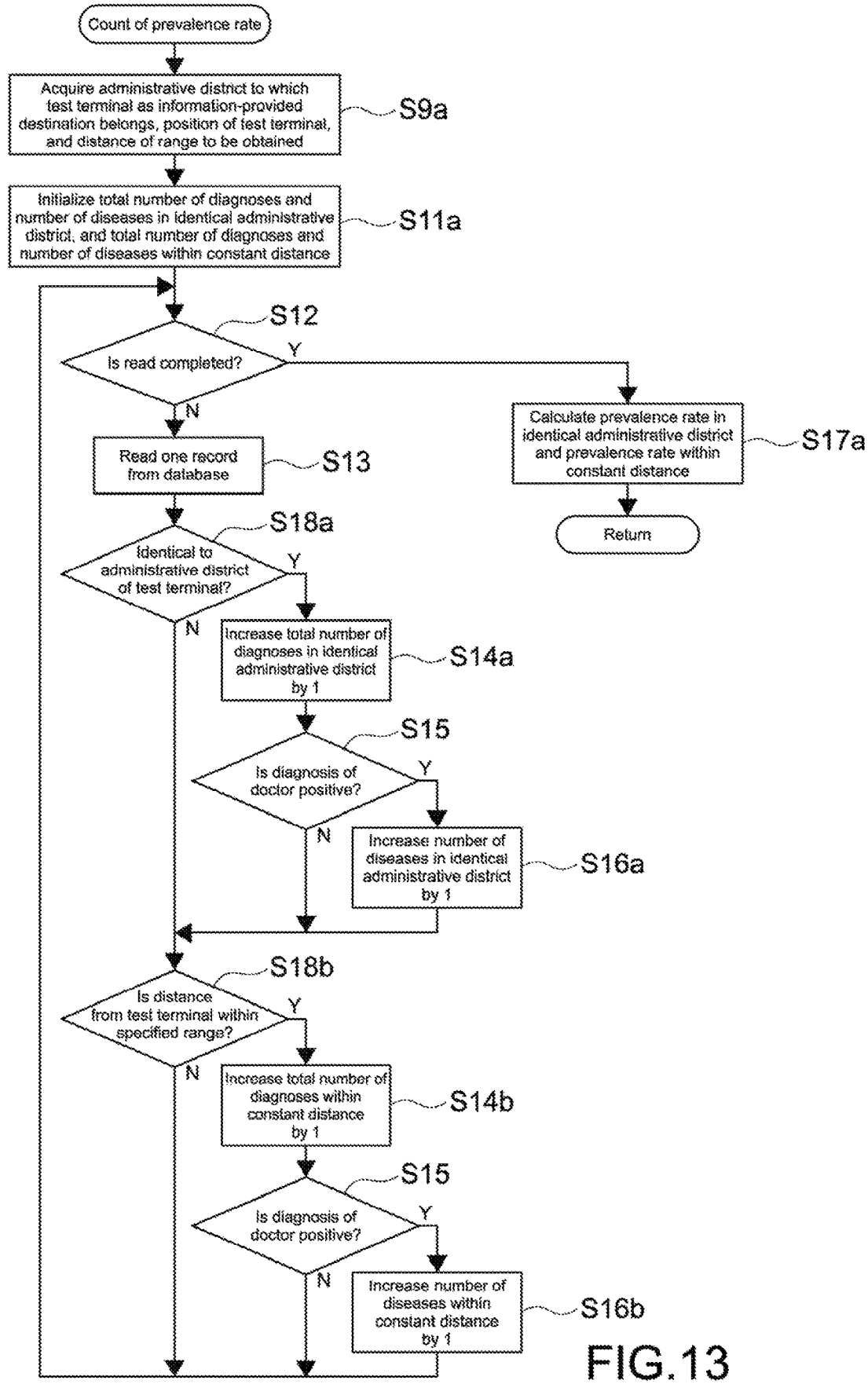
FIG. 13 is a flowchart for describing processing to count and calculate a prevalence rate after narrowing down count target data based on an administrative district and a physical distance, in processing to count and calculate a prevalence rate.

FIG. 13 is a flowchart for describing processing to count and calculate the prevalence rate after narrowing down count target data based on an administrative district and a physical distance, in the above-mentioned processing to count and calculate the prevalence rate.

First, the CPU 41 of the test server 40 acquires, from a test terminal 20 to be an information-provided destination of the prevalence rate or the like, an administrative district to which the test terminal 20 belongs, a current position, and a physical distance (radius) of a desired range (Step S9*a*).

Next, the CPU 41 clears the total number of diagnoses and the number of diseases in an identical administrative district, and the total number of diagnoses of test results in the range of a specified distance and the number of diseases, to zero for initialization (Step S11*a*). The total number of diagnoses and the number of diseases in an identical administrative district, and the total number of diagnoses of test results in the range of a specified distance and the number of diseases are variables used for count up at the time of count.

Next, the CPU 41 determines whether all records of the database 47*a* are read or not (Step S12).

At this moment, since all the records of the database 47*a* are not yet read (N of Step S12), the CPU 41 then reads one record from the database 47*a* (Step S13).

Next, the CPU 41 determines whether the administrative district of the read record is identical to the administrative district of the test terminal 20 or not (Step S18*a*). It should be noted that the item "Administrative District" used here can be derived as a part of the item "Address" in the database 47*a*.

In the case where the administrative district of the read record is identical to the administrative district of the test terminal 20 (Y of Step S18*a*), the CPU 41 then counts up the total number of diagnoses in the identical administrative district by 1 (Step S14*a*).

Next, the CPU 41 determines whether "Diagnosis" of the doctor, which is one field of the read record, is positive or not (Step S15).

Only in the case where the result is positive (Y of Step S15), the CPU 41 counts up the number of diseases in the identical administrative district by 1 (Step S16*a*).

In the case where the administrative district of the read record is different from the administrative district of the test terminal 20 in Step 18*a* (N of Step S18*a*), in the case where the result is negative in Step S15 (N of Step S15), or after the number of diseases is counted up in Step S16*a*, the CPU 41 advances the processing to Step S18*b* and continues the processing.

Next, the CPU 41 determines whether a distance between a position at which a test in the read record is performed and the current position of the test terminal 20 falls within the specified range or not (Step S18*b*).

In the case where the distance falls within the specified range (Y of Step S18*b*), the CPU 41 then counts up the total number of diagnoses within the specified distance by 1 (Step S14*b*).

Next, the CPU 41 determines whether "Diagnosis" of the doctor, which is one field of the read record, is positive or not (Step S15).

Only in the case where the result is positive (Y of Step S15), the CPU 41 counts up the number of diseases within the specified distance by 1 (Step S16*b*).

In the case where the distance does not fall within the specified range in Step 18*b* (N of Step S18*b*), in the case where the result is negative in Step S15 (N of Step S15), or after the number of diseases is counted up in Step S16*b*, the CPU 41 returns the processing back to Step S12 and continues the processing.

In Step S12, in the case where all the records of the database 47*a* are completely read (Y of Step S12), according to the mathematical expression (6), the CPU 41 then calculates the prevalence rate in the identical administrative district from the total number of diagnoses and the number of diseases in the identical administrative district, and calculates the prevalence rate within the specified range from the total number of diagnoses and the number of diseases within the specified range (Step S17*a*).

Hereinbefore, the configuration in which test results to be the basis for counting and calculating the prevalence rate are narrowed down based on the attribute of the test terminal 20 has been described.

Modified Example 7 Narrowing-Down of Target Data Based on Patient Attribute

In the above modified example in which narrowing-down is performed, the configuration has been described in which test results to be the basis for counting and calculating the prevalence rate are narrowed down based on the attribute of the test terminal 20. In contrast to this, in a modified example to be described here, a configuration will be described in which test results to be the basis for counting and calculating the prevalence rate are narrowed down based on the attribute of a patient who is subjected to a test (patient attribute information), instead of the attribute of the test terminal 20.

In the example described here, test results to be counted are narrowed down based on the gender or age of a patient who is subjected to a test with the test terminal 20 that demands a prevalence rate, to count and calculate the prevalence rate. However, an example of narrowing-down to be described here is different from the above-mentioned narrowing-down based on the attribute of the test terminal 20, and is exactly a sorting on an attribute content basis.

For example, in narrowing-down by gender, count is not performed based on only gender identical to that of the patient, but performed based on male and female, and respective values are held. In the case where the prevalence rate of a gender is required, the test server 40 collects the prevalence rates of males and females and provides the prevalence rates to the test terminal 20.

It should be noted that as in the example of the above-mentioned narrowing-down based on the attribute of the test terminal 20, it is needless to say that the following configuration is adopted: gender information of a patient who is subjected to a test is first acquired, records of the gender of male only are extracted from the database 47*a* for counting, and then only a prevalence rate of male is calculated. In the case of calculating a prevalence rate related to an attribute that is less common and is not demanded by the test terminal 20 frequently, it is effective to perform extraction related to that attribute each time such a demand is generated.

As described above, performing various types of narrowing-down when the prevalence rate is calculated allows more adequate information to be provided to individual patients.

Figure 14:
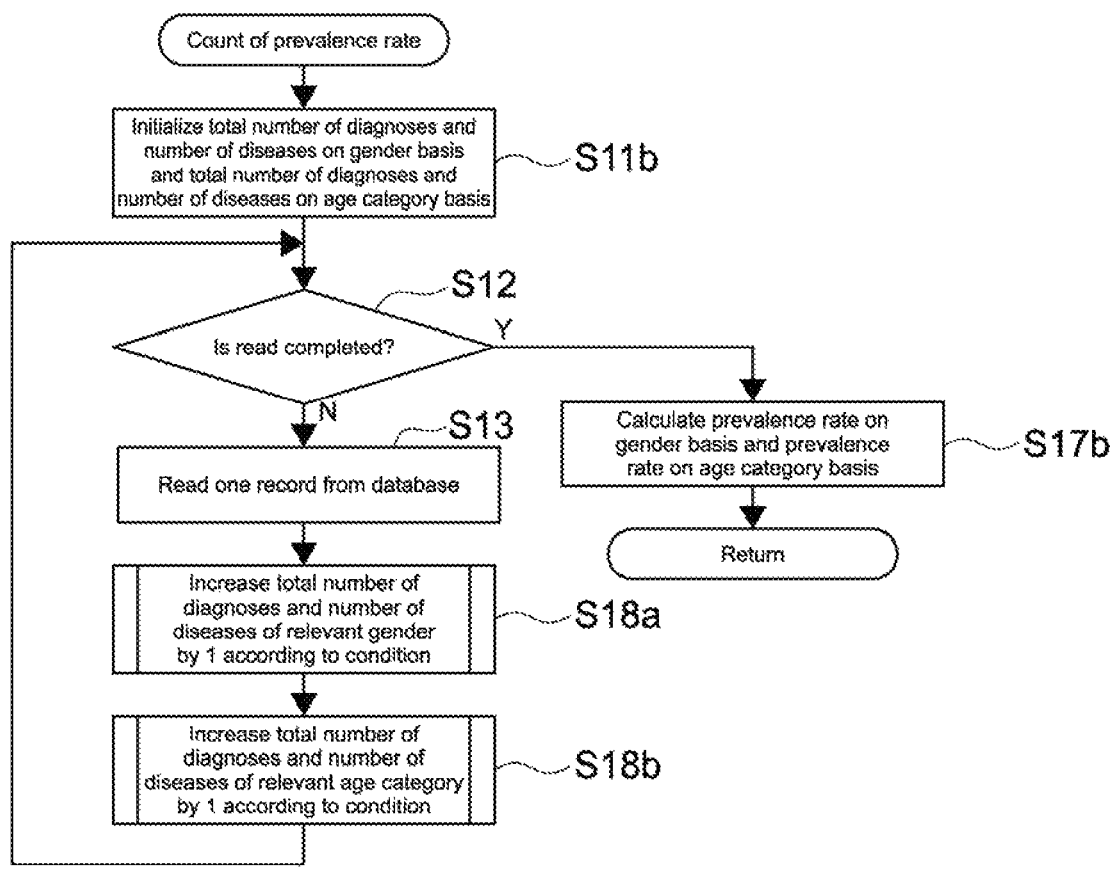
FIG. 14 is a flowchart for describing the processing to count and calculate a prevalence rate after narrowing down count target data based on gender and an age category of patients, in the processing to count and calculate a prevalence rate.

FIG. 14 is a flowchart for describing processing to count and calculate the prevalence rate after narrowing down count target data based on gender and an age category (for example, categories on a ten-year basis, such as the ages of 0 to 9 and the ages of 10 to 19) of patients, in the processing to count and calculate the prevalence rate described above. It should be noted that in the description of this flowchart, processing similar to the above-mentioned narrowing-down based on the attribute of the test terminal 20 will not be described.

First, the CPU 41 of the test server 40 clears variables of the total number of diagnoses and the number of diseases, on an attribute category basis, to zero for initialization (Step S11b). The variables are used for count up at the time of count.

Next, the CPU 41 determines whether all records of the database 47a are read or not (Step S12).

At this moment, since all the records of the database 47a are not yet read (N of Step S12), the CPU 41 then reads one record from the database 47a (Step S13).

Next, the CPU 41 counts up the total number of diagnoses and the number of cases determined to be positive, on a gender category basis (Step S18a).

Next, the CPU 41 counts up the total number of diagnoses and the number of cases determined to be positive, on an age category basis (Step S18b). The CPU 41 then returns the processing back to Step S12 and continues the processing.

In Step S12, in the case where all the records of the database 47a are completely read (Y of Step S12), the CPU 41 then calculates the prevalence rate on an attribute category basis, from the total number of diagnoses and the number of diseases on an attribute category basis (Step S17b).

It should be noted that here, the gender and the age are exemplified as the attributes of patients, but the narrowing-down may be performed using an attribute other than those above attributes. At that time, it is assumed that an item corresponding to that attribute is provided in the records of the database 47a and data corresponding to that item is accumulated.

Examples of other attributes of patients include (1) medical interview information, (2) current and past medication information, (3) previous disease, (4) physical information such as a body temperature, a blood pressure, and a body weight, (5) information on lifestyle habits, such as an exercise volume, a volume or kinds of food, and a sleep length.

Further, examples of still other attributes of patients include (6) genotypes of germline and somatic line genes, including Genomic Variants, SNPs (Single Nucleotide Polymorphism), GWAS (Genome-wide Association Study), indel (insertion-deletion), CNV (Copy Number Variation), mRNA (messenger RNA), Epigenetics, miRNA (microRNA), and the like of the genes.

Further, attributes such as (7) microbial flora (intestinal bacteria and the like) of patients and (8) race can also be used.

Hereinbefore, the configuration in which test results to be the basis for counting and calculating the prevalence rate are narrowed down based on the attribute of a patient who is subjected to a test, instead of the attribute of the test terminal 20.

(Modified Example 8 Case Where Narrowing-Down Based on Patient Attribute is not Enabled)

In the modified example in which the above-mentioned narrowing-down is performed, the narrowing-down is performed using the attribute of the test terminal 20 or the attribute of patients. In contrast to this, in a modified example to be described here, one of solutions to a case where the number of target test results becomes insufficient as a result of the narrowing-down and a meaningful prevalence rate cannot be derived from the count of the test results will be described.

In a solution described here, a prevalence rate that is obtained from all cases in the database 47a before narrowing-down is performed is corrected based on correction information acquired from outside the test system 10, and thus a prevalence rate in the case of narrowing-down under a target condition is calculated.

It should be noted that in the following description, a genetic polymorphism among attributes of patients will be described as a condition for narrowing-down.

Figure 15:
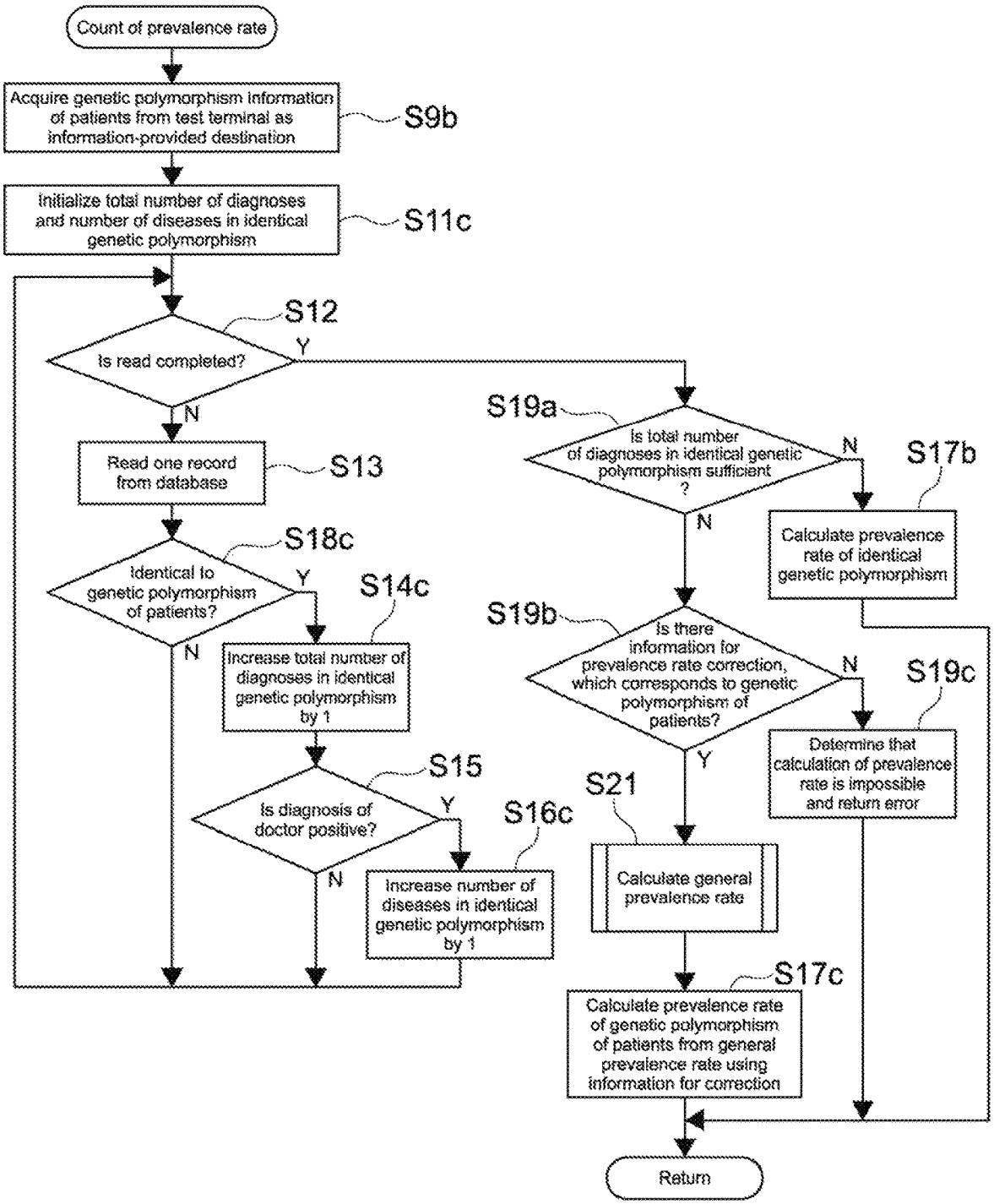
FIG. 15 is a flowchart of processing to calculate, in the case where the number of registered patients is small in the database 47a and narrowing-down according to a genetic polymorphism is meaningless, a prevalence rate of that genetic polymorphism by correcting the overall prevalence rate using a predetermined sensitivity.

FIG. 15 is a flowchart of processing to calculate, in the case where the number of registered patients is small in the database 47a and narrowing-down according to a genetic polymorphism is meaningless, a prevalence rate for that genetic polymorphism by correcting the overall prevalence rate using a predetermined sensitivity. In other words, when the number of patients having the genetic polymorphism is not sufficiently registered in the test server 40 but there is sensitivity correction information for calculating a prevalence rate for that genetic polymorphism, the prevalence rate for that genetic polymorphism is calculated from the overall prevalence rate by correction.

First, the CPU 41 of the test server 40 acquires genetic polymorphism information of patients, which is input to the test terminal 20 as an information-provided destination (Step S9b). It should be noted that the genetic polymorphism information of patients may be directly input to the test terminal 20 or may be acquired from outside, such as another server, based on a Patient ID received from the test terminal.

Next, the CPU 41 clears variables of the total number of diagnoses and the number of diseases in an identical genetic polymorphism to zero for initialization (Step S11c). The variables are used for count up at the time of count.

Next, the CPU 41 determines whether all records of the database 47a are read or not (Step S12).

At this moment, since all the records of the database 47a are not yet read (N of Step S12), the CPU 41 then reads one record from the database 47a (Step S13).

Next, the CPU 41 determines whether a genetic polymorphism of the read record and a genetic polymorphism acquired from the test terminal 20 are identical or not (Step S18c).

In the case where the genetic polymorphisms are identical to each other (Y of Step S18c), the CPU 41 then counts up the total number of diagnoses in the identical genetic polymorphism by 1 (Step S14c).

Next, the CPU 41 determines whether "Diagnosis" of the doctor, which is one field of the read record, is positive or not (Step S15).

Only in the case where the result is positive (Y of Step S15), the CPU 41 counts up the number of diseases in the identical genetic polymorphism by 1 (Step S16c).

In the case where the genetic polymorphisms are different from each other in Step 18c (N of Step S18c), in the case where the result is negative in Step S15 (N of Step S15), or after the number of diseases is counted up in Step S16c, the CPU 41 returns the processing back to Step S12 and continues the processing.

In Step S12, in the case where all the records of the database 47a are completely read (Y of Step S12), the CPU 41 then determines whether the total number of diagnoses in the identical genetic polymorphism is sufficient or not (Step S19a).

In the case where the total number is sufficient (Y of Step S19a), the CPU 41 calculates a prevalence rate in an identical genetic polymorphism based on the total number of diagnoses and the number of diseases in the identical genetic polymorphism (Step S17b).

In the case where the total number is not sufficient (N of Step S19a), the CPU 41 then determines whether there is information for prevalence rate correction, which corresponds to the genetic polymorphism of patients (Step S19b).

In the case where there is no information for prevalence rate correction (N of Step S19b), the CPU 41 determines that a calculation of a prevalence rate corresponding to the genetic polymorphism of patients is impossible, and then returns an error (Step S19c).

In the case where there is information for prevalence rate correction (Y of Step S19b), the CPU 41 then calculates a prevalence rate (general prevalence rate) in the case where test results are not narrowed down to an identical genetic polymorphism (Step S21).

Next, the CPU 41 corrects the calculated general prevalence rate using the information for prevalence rate correction (sensitivity information), to calculate the prevalence rate in the genetic polymorphism of patients (Step S17c).

As described above, even if the number of patients having the transmitted genetic polymorphism is not sufficiently registered in the test server 40, in the case where there is sensitivity information used for prevalence rate correction, which corresponds to that genetic polymorphism, the corrected prevalence rate can be returned to the test terminal.

It should be noted that in the above description, the correction value for correcting a general prevalence rate is acquired from outside, but the present technology is not limited thereto. A prevalence rate corresponding to each category of a terminal attribute and a patient attribute may be acquired from outside. For example, prevalence rate information on a gender or age category basis may be acquired from outside in the format of XML (eXtended Markup Language) or the like.

Figure 16:
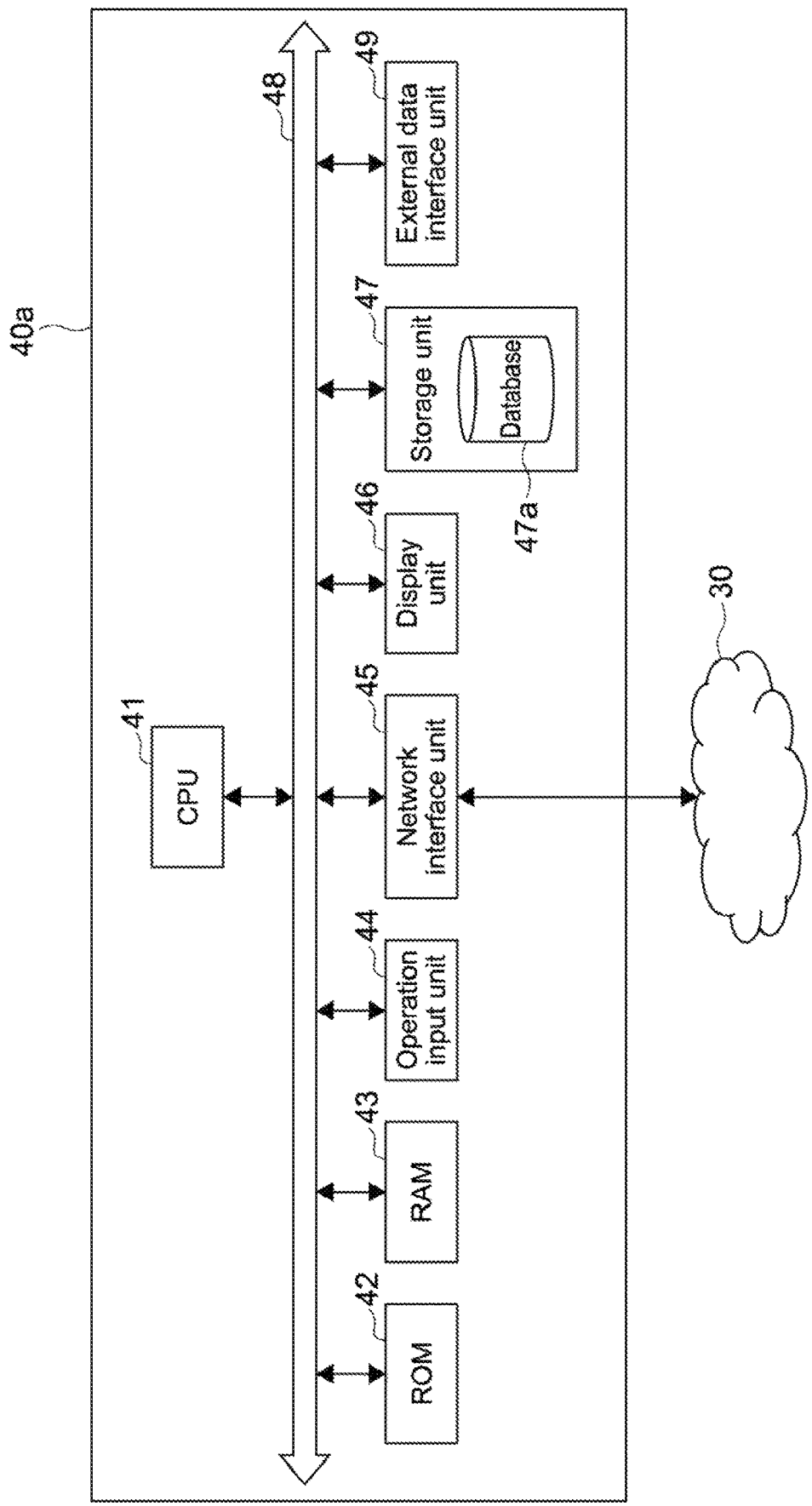
FIG. 16 is a block diagram showing a configuration example of a test server 40a that can correct the prevalence rate using sensitivity information.

Next, a configuration of a test server 40a used in this modified example will be described. FIG. 16 is a block diagram showing a configuration example of the test server 40a that can correct the prevalence rate using the sensitivity information described above. The difference from the test server 40 described above is an external data interface unit 49 additionally provided.

The sensitivity information used for correction based on a disease and a genetic polymorphism is input by the user via the operation input unit 44 or acquired from a memory card or the like storing the sensitivity information, via the external data interface unit 49. It should be noted that the sensitivity information may be acquired via the network interface unit 45 over the network 30.

Acquiring the sensitivity information for correction allows the test server 40a to correct a prevalence rate and provide a prevalence rate corresponding to a specific genetic polymorphism during operation of a service for providing a prevalence rate and the like.

Modified Example 9 Correction of Prevalence Rate by Weighting

In the above description, the configuration has been described in which the weight of one test result is counted as 1 (the number of positive cases is simply counted) when the count for calculating a prevalence rate is performed. In contrast to this, in a modified example to be described here, the following configuration will be described in which the number of counted-up positive cases is weighted for correction, to predict a true prevalence rate, in consideration of an environmental condition where a test is performed (for example, immunization penetration rate in a specific region). It should be noted that the weighting is performed by multiplication of a coefficient according to a predetermined condition, for example.

Figure 17:
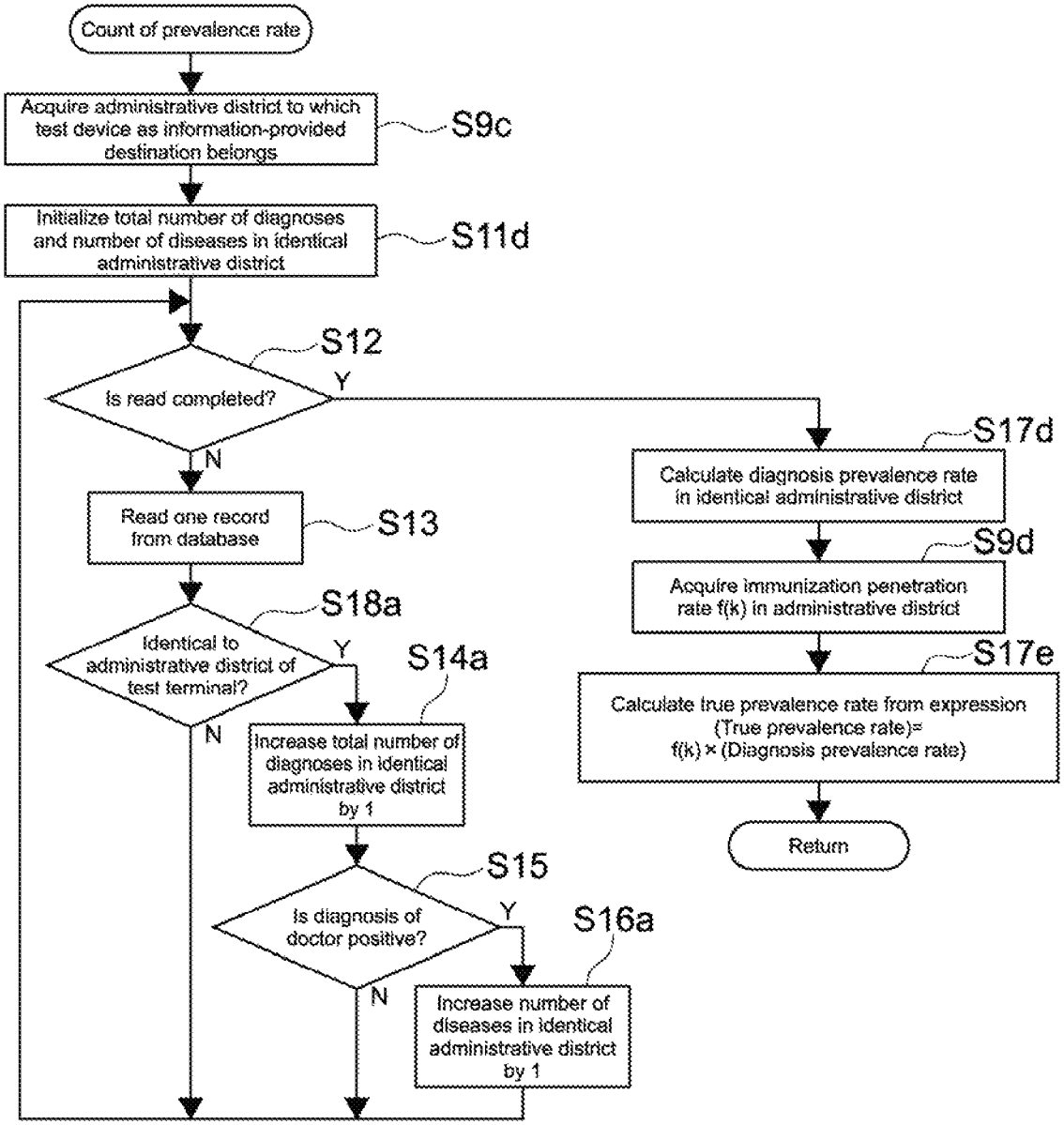
FIG. 17 is a flowchart of processing to perform weighting correction on the prevalence rate (diagnosis prevalence rate) calculated by count of the database 47a in a certain administrative district, based on an immunization penetration rate in that administrative district, to predict a true prevalence rate.

FIG. 17 is a flowchart of processing to perform weighting correction on the prevalence rate (diagnosis prevalence rate) calculated by the count of the database 47a in a certain administrative district, based on the immunization penetration rate in that administrative district, to predict a true prevalence rate. It should be noted that in the processing described here, the following mathematical expression (14) is assumed to be established using an immunization penetration rate f(k).

$$\text{(predicted true prevalence rate)} = f(k) \times \text{(diagnosis prevalence rate)} \quad (14)$$

Further, a specific value of the immunization penetration rate f(k) is assumed to be calculated based on a relationship between a true prevalence rate determined in the past and a diagnosis prevalence rate calculated in the past, using the mathematical expression (14).

First, the CPU 41 of the test server 40 acquires, from a test terminal 20 to be a destination provided with information such as a prevalence rate, an administrative district to which that test terminal 20 belongs (Step S9c).

Next, the CPU 41 clears the total number of diagnoses and the number of diseases in an identical administrative district to zero for initialization (Step S11d). The total number of diagnoses and the number of diseases in an identical administrative district are variables used for count up at the time of count.

Next, the CPU 41 determines whether all records of the database 47a are read or not (Step S12).

Here, the processing in Steps S13, S18a, S14a, S15, and S16a, which is performed by the time all the records of the database are completely read, is the same as the processing described above and is for calculating the total number of diagnoses and the number of diseases in an identical administrative district. Description of the processing will thus be omitted.

In Step S12, in the case where all the records of the database 47a are completely read (Y of Step S12), the CPU 41 then calculates a prevalence rate (diagnosis prevalence rate) in the identical administrative district from the total number of diagnoses and the number of diseases in the identical administrative district according to the mathematical expression (6) (Step S17d).

Next, the CPU 41 acquires an immunization penetration rate f(k) in the administrative district to which the test terminal 20 belongs (Step S9d). It should be noted that the CPU 41 may preliminarily hold information of the immunization penetration rate f(k) in the test server 40 or acquire the information from outside the test system 10. Further, the value of the immunization penetration rate f(k) may be updated in the test server 40 as needed.

Next, the CPU 41 calculates a predicted true prevalence rate using the mathematical expression (14) (Step S17e). The predicted true prevalence rate calculated here is replaced with the prevalence rate described above, and the following processing is performed.

In the above description, the administrative district is used as a condition of weighting. In addition thereto, examples of characteristics of the region as a condition of weighting include a country, a population, a population density, a position of the test terminal 20, a distance from the test terminal 20, uniqueness of an environment, a poverty level, a traffic situation around the test terminal 20, and a population change per day around the test terminal 20.

As found from the narrowing-down conditions used in the modified example of narrowing-down described above and the weighting conditions used in the modified example of weighting described here, conditions such as an administrative district can be used for narrowing-down and weighting.

It should be noted that in the above description, the weighting based on the attribute of the test terminal 20 has been described, but the weighting may be performed based on patient attributes, for example, attributes such as a body temperature, a blood pressure, and a gene type of a patient.

Hereinbefore, the configuration has been described in which the number of counted-up positive cases is weighted for correction, to predict a true prevalence rate, in consideration of an environmental condition where a test is performed.

(Modified Example 10 Substitute Index of Prevalence Rate when Diagnosis is Unavailable (Part 1))

In the above description, it is assumed that a diagnosis of a doctor is also certainly obtained in the past test result in order to calculate a prevalence rate. In contrast to this, in a modified example to be described here, it is assumed that a final diagnosis of a doctor may not be sometimes input when a test is performed with the test terminal 20. When a final diagnosis of a doctor may not be sometimes input, a blank is generated in the "Diagnosis" column of the database 47a, and the degree of accuracy of a prevalence rate to be collected and obtained is reduced. In this regard, in this modified example, an approximate index to serve as a substitute for the prevalence rate is used instead of the prevalence rate.

For example, it is conceived that the positive rate is used as the approximate index. As found from the following mathematical expression (15), the positive rate can be obtained from the number of test positive cases, which can be automatically acquired, when a test is performed with the test terminal 20. For that reason, even in the case where a record in which a final diagnosis of a doctor is not input exists in the database 47a and a calculation for a prevalence rate is not appropriately performed, using an index substituted by the positive rate allows an approximate value of an adequate prevalence rate to be provided to the test terminal 20.

$$(\text{positive rate}) = (\text{number of test positive cases})/(\text{total number of diagnoses}) \quad (15)$$

It should be noted that a point of the following processing is that even when the number of records in which a diagnosis of a doctor is input to the database 47a is insufficient, when the prevalence rate falls within a range capable of being replaced with the positive rate and the number of records having positive test results is enough, the positive rate is substituted for the prevalence rate.

Figure 18:
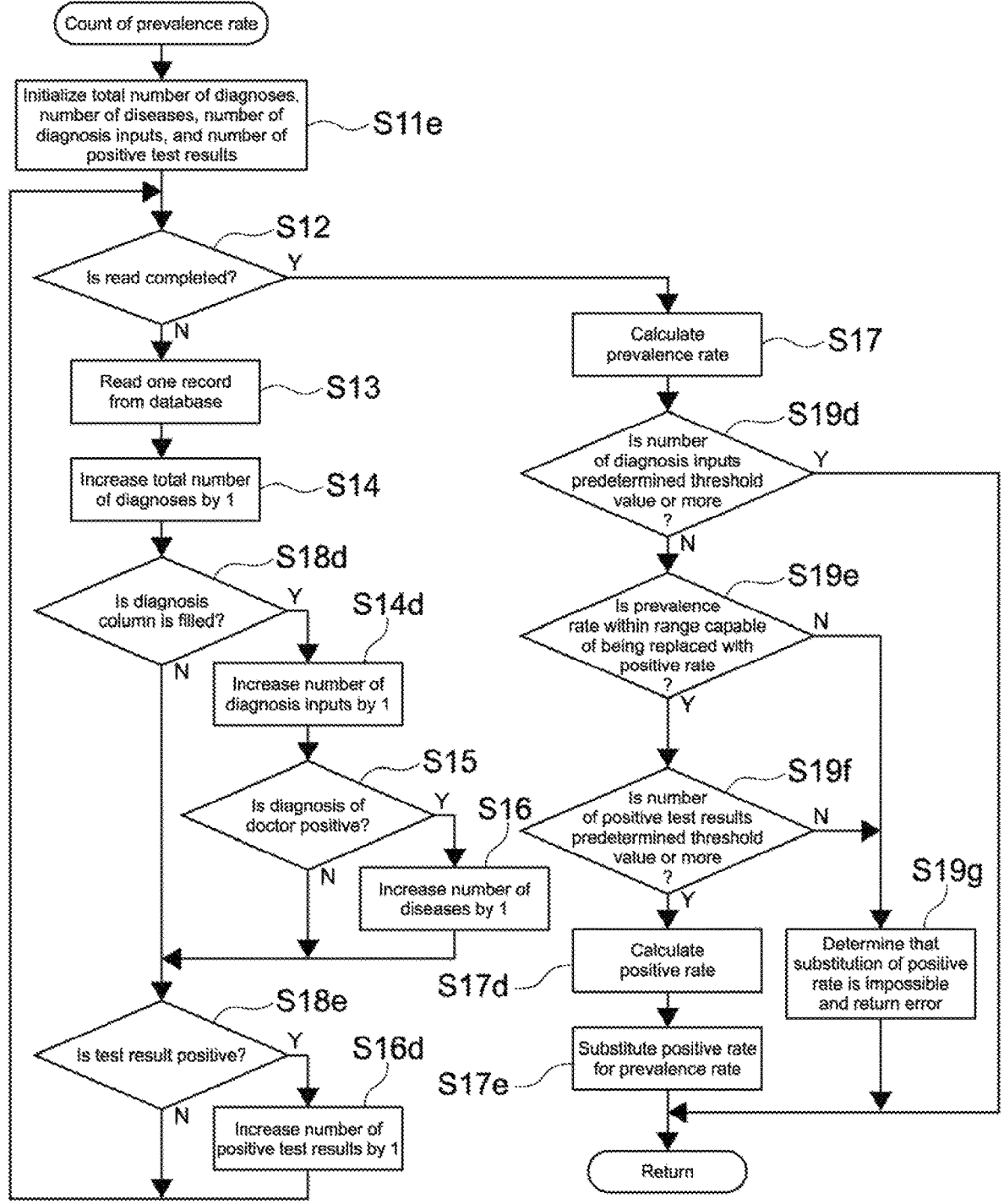
FIG. 18 is a flowchart for describing processing using an approximate index to be a substitute for the prevalence rate, instead of the prevalence rate.

FIG. 18 is a flowchart for describing processing using an approximate index to be a substitute for the prevalence rate, instead of the prevalence rate.

First, the CPU 41 of the test server 40 clears the total number of diagnoses, the number of diseases, the number of diagnosis inputs, and the number of positive test results to zero for initialization (Step S11e). The total number of diagnoses, the number of diseases, the number of diagnosis inputs, and the number of positive test results are variables used for count up at the time of count.

Next, the CPU 41 determines whether all records of the database 47a are read or not (Step S12).

At this moment, since all the records of the database 47a are not yet read (N of Step S12), the CPU 41 then reads one record from the database 47a (Step S13).

Next, the CPU 41 then counts up the total number of diagnoses by 1 (Step S14).

Next, the CPU 41 determines whether the "Diagnosis" column of a doctor, which is one field of the read record, is filled or not (Step S18d).

In the case where the "Diagnosis" column is filled (Y of Step S18d), the CPU 41 then counts up the number of diagnosis inputs by 1 (Step S14d).

Next, the CPU 41 determines whether the "Diagnosis" of the doctor, which is one field of the read record, is positive or not (Step S15).

In the case where the diagnosis is positive (Y of Step S15), the CPU 41 counts up the number of diseases by 1 (Step S16).

In the case where the "Diagnosis" column is not filled in Step S18d (N of Step S18d), in the case where the diagnosis is negative in Step S15 (N of Step S15), or after the number of diseases is counted up in Step S16, the CPU 41 advances the processing to Step S18e and continues the processing.

Next, the CPU 41 determines whether a test result of the test device 28 is positive or not (Step S18e).

Only in the case where the test result is positive (Y of Step S18e), the CPU 41 counts up the number of positive test results by 1 (Step S16d).

In the case where the test result is negative in Step S18e (N of Step S18e) or after the number of diseases is counted up in Step S16d, the CPU 41 returns the processing back to Step S12 and continues the processing.

In Step S12, in the case where all the records of the database 47a are completely read (Y of Step S12), the CPU 41 calculates a prevalence rate from the total number of diagnoses and the number of diseases according to the mathematical expression (6) (Step S17).

Next, the CPU 41 determines whether the number of diagnosis inputs is a predetermined threshold value or more (Step S19d).

In the case where the number of diagnosis inputs is a predetermined threshold value or more (Y of Step S19d), the prevalence rate calculated in Step S17 is considered as an adequate value and used in the following processing.

In the case where the number of diagnosis inputs is less than a predetermined threshold value (N of Step S19d), the prevalence rate calculated in Step S17 is considered as an inadequate value for use in the following processing. The CPU 41 then determines whether the calculated prevalence rate falls within a range capable of being replaced with the positive rate or not (Step S19e).

In the case where the calculated prevalence rate falls within a range capable of being replaced with the positive rate (Y of Step S19e), the CPU 41 then determines whether the number of positive test results is a predetermined threshold value or more (Step S19f).

In the case where the number of positive test results is a predetermined threshold value or more (Y of Step S19f), the CPU 41 then calculates a positive rate using the mathematical expression (15) (Step S17d).

Next, the CPU 41 substitutes the positive rate for the prevalence rate (Step S17e). The positive rate is substituted for the value of the prevalence rate and used in the following processing.

It should be noted that in the case where the prevalence rate does not fall within a range capable of being replaced with the positive rate in Step S19e (N of Step S19e) and in the case where the number of positive test results is less than the predetermined threshold value in Step S19f (N of Step S19f), the CPU 41 determines that a substitution of the positive rate for the prevalence rate is impossible, and then returns an error (Step S19g).

Hereinbefore, the modified example in which an approximate index to serve as a substitute for the prevalence rate is used instead of the prevalence rate has been described.

(Regarding Relationship Between Prevalence Rate and Positive Rate in Specific Sensitivity/Specifity)

Here, the fact that the relationship between the prevalence rate and the positive rate changes based on the sensitivity and the specificity will be described.

Figure 19:
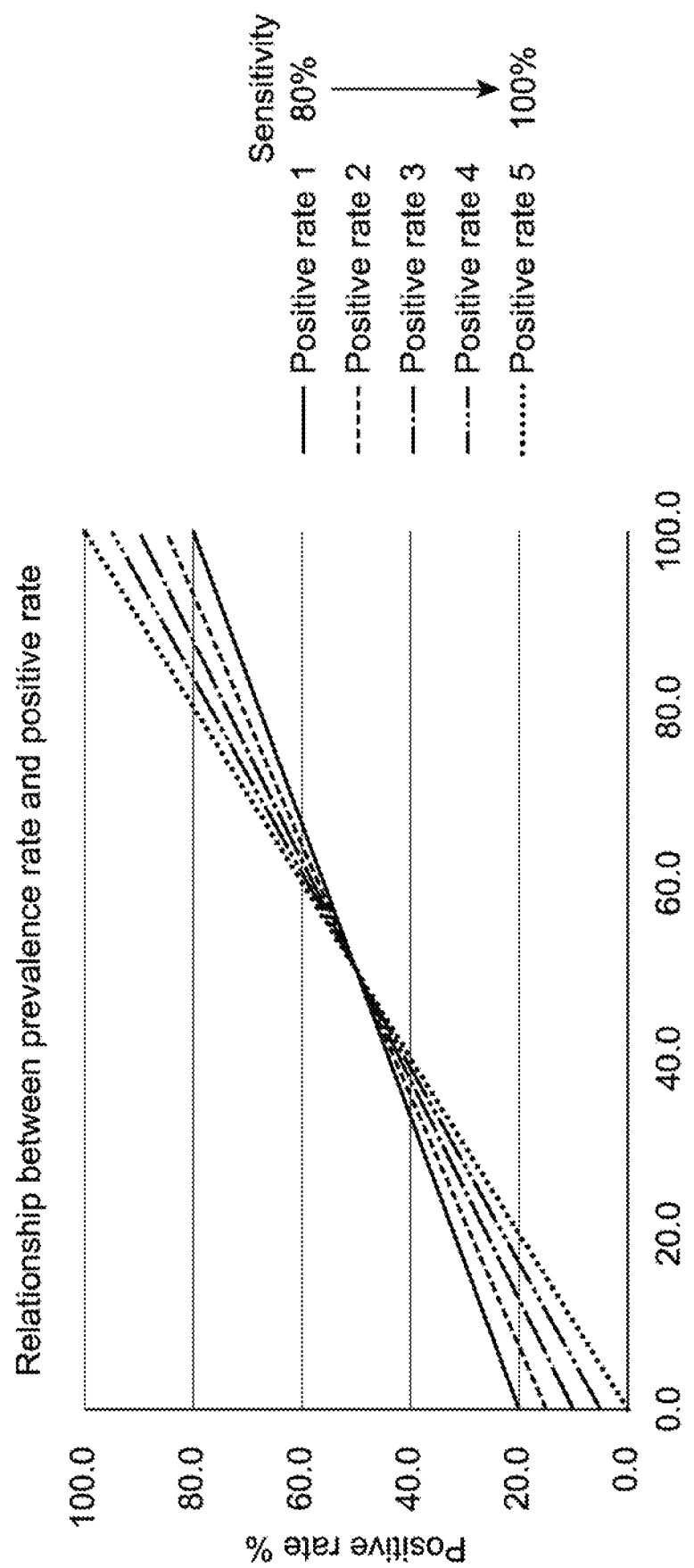
FIG. 19 is a graph showing a relationship between a prevalence rate and a positive rate when the sensitivity and the specificity are changed.

FIG. 19 is a graph showing the relationship between the prevalence rate and the positive rate when the sensitivity and the specificity are changed. This figure shows the relationship between the prevalence rate and the positive rate, when the sensitivity and the specificity of the diagnosis device 28 are changed, by 5%, from 80% (line indicated by a positive rate 1) to 85% (line indicated by a positive rate 2), 90% (line indicated by a positive rate 3), 95% (line indicated by a positive rate 4), and 100% (line indicated by a positive rate 5).

As found from this graph, as the sensitivity/specificity are increased, the prevalence rate and the positive rate becomes matched, starting from the line of positive rate 1 in which the most mismatched relationship between the prevalence rate and the positive rate is shown, and in the line of positive rate 5, the prevalence rate and the positive rate are matched. This shows that a positive rate based on a test result obtained with a diagnosis device having a higher sensitivity and specificity shows a value closer to the prevalence rate.

In other words, a positive rate based on a test result of a higher sensitivity/high specificity test can present a more correct positive predictive value and negative predictive value to the user.

Figure 20:
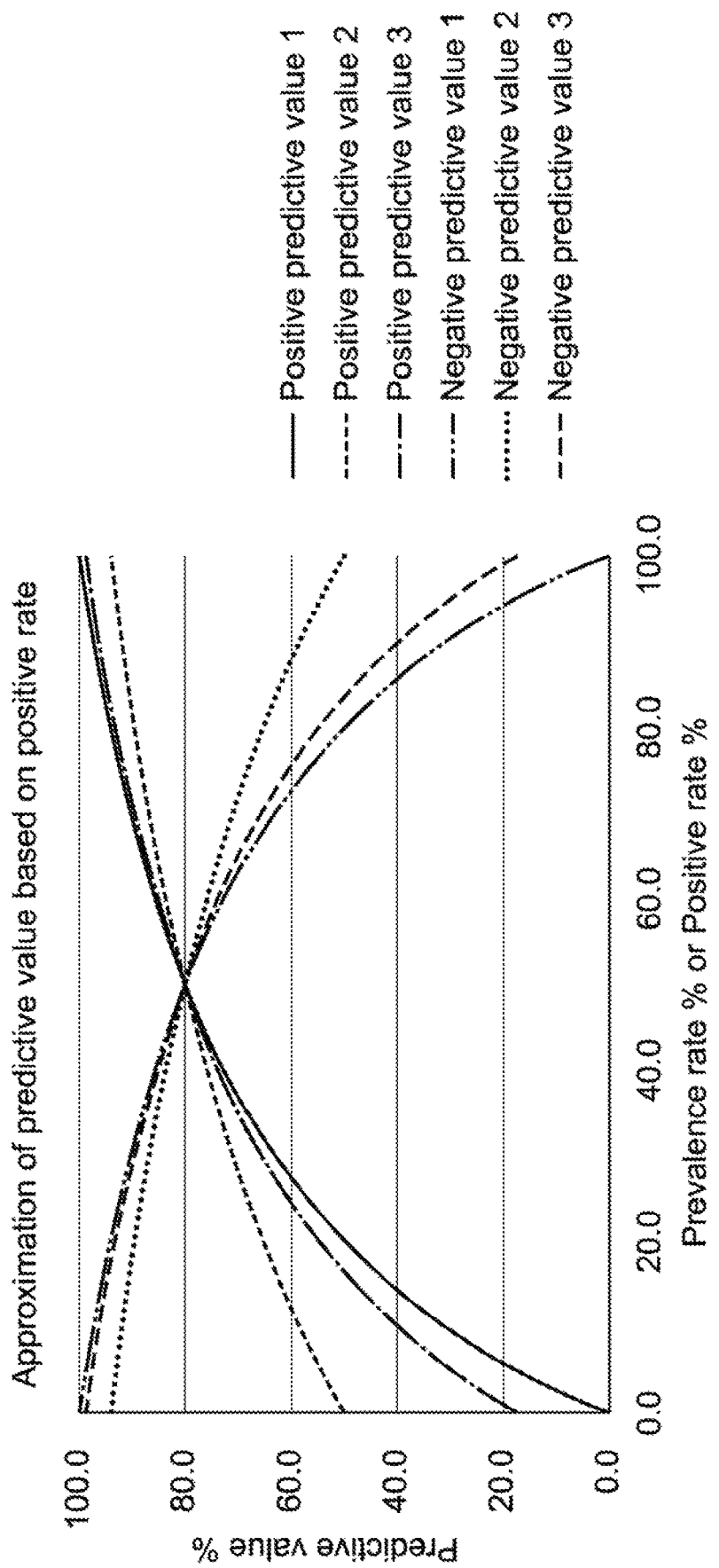
FIG. 20 is a graph showing a relationship between a prevalence rate or a positive rate as a substitute for the prevalence rate, and the positive predictive value and the negative predictive value.

Here, the positive predictive value and the negative predictive value in the case where the positive rate is used instead of the prevalence rate will be described. FIG. 20 is a graph showing a relationship between a prevalence rate or a positive rate as a substitute for the prevalence rate, and the positive predictive value and the negative predictive value.

Found in this graph is a relationship between a prevalence rate (or positive rate), and a positive predictive value and negative predictive value to be calculated, when a test is performed with a test device 28 having a sensitivity of 80% and a specificity of 80%. Lines of a positive predictive value 1 and a negative predictive value 1 represent a positive predictive value and a negative predictive value that are calculated using an original prevalence rate.

Lines of a positive predictive value 2 and a negative predictive value 2 represent a positive predictive value and a negative predictive value that are calculated in the case of using a positive rate of another test with a sensitivity of 80% and a specificity of 80% instead of the prevalence rate. Further, lines of a positive predictive value 3 and a negative predictive value 3 represent a positive predictive value and a negative predictive value that are calculated in the case of using a positive rate of another test with a sensitivity of 95% and a specificity of 95% instead of the prevalence rate.

For example, a line of a positive predictive value 3 (sensitivity/specificity of 95%) is approximate to the line of the positive predictive value 1 as an original positive predictive value, compared with the line of the positive predictive value 2 (sensitivity/specificity of 80%).

As described above, in the case where the positive rate is substituted for the prevalence rate, using a positive rate based on a diagnosis device having a higher sensitivity and a higher specificity leads to obtaining a positive predictive value and a negative predictive value that are more approximate to the positive predictive value and negative predictive value calculated from the original prevalence rate. This is more effective.

Hereinbefore, the fact that the relationship between the prevalence rate and the positive rate is changed based on the sensitivity and the specificity has been described.

Modified Example 11 Substitute Index of Prevalence Rate When Diagnosis is Unavailable (Part 2)

In the above modified example in which the positive rate is substituted for the prevalence rate, a positive rate obtained by a certain test method is used instead of a prevalence rate for the test method. In contrast to this, in the case where the positive rate is substituted for the prevalence rate as described above, using a positive rate based on a diagnosis device having a higher sensitivity and a higher specificity leads to obtaining a positive predictive value and a negative predictive value that are more approximate to the positive predictive value and negative predictive value calculated from the original prevalence rate. This point is considered in this modified example. It should be noted that a higher sensitivity and a higher specificity used here mean that they are sufficiently high enough to be credible, in other words, mean that a predetermined value preliminarily demanded is satisfied.

In this regard, in the configuration of this modified example, on the assumption that test results based on a plurality of test methods using different sensitivities and specificities are stored in the database 47a, in the case where another index has to be substituted for the prevalence rate on a test method (first test method) using a low sensitivity/specificity, a positive rate on a test method (second test method) using high numerical values of the sensitivity/specificity is used As an example in which such a configuration may be adopted, a test of influenza virus is exemplified. Examples of a test method for influenza virus include immunochromatography of a low sensitivity/specificity and a PCR (Polymerase Chain Reaction) method of a high sensitivity/specificity.

In the case where the prevalence rate is difficult to calculate by immunochromatography because a diagnosis of a doctor is not yet input, a positive rate by the PCR method is used as a substitute for the prevalence rate. This allows a calculation of values that are more approximate to the original positive predictive value and negative predictive value even in the case where the prevalence rate is difficult to calculate by the immunochromatography.

It should be noted that the positive predictive value and the negative predictive value to be calculated are represented by the following mathematical expressions (16) and (17), using a sensitivity (sensitivity i) and a specificity (specificity i) by the immunochromatography and a positive rate (positive rate p) by the PCR method.

$$\text{positive predictive value} = \text{sensitivity } i \times \text{positive rate } p/(\text{sensitivity } i \times \text{positive rate } p + (1 - \text{positive rate } p)(1 - \text{specificity } i)) \quad (16)$$

$$\text{negative predictive value} = \text{specificity } i \times (1 - \text{positive rate } p)/(\text{specificity } i \times (1 - \text{positive rate } p) + \text{positive rate } p \times (1 - \text{sensitivity } i)) \quad (17)$$

Figure 21:
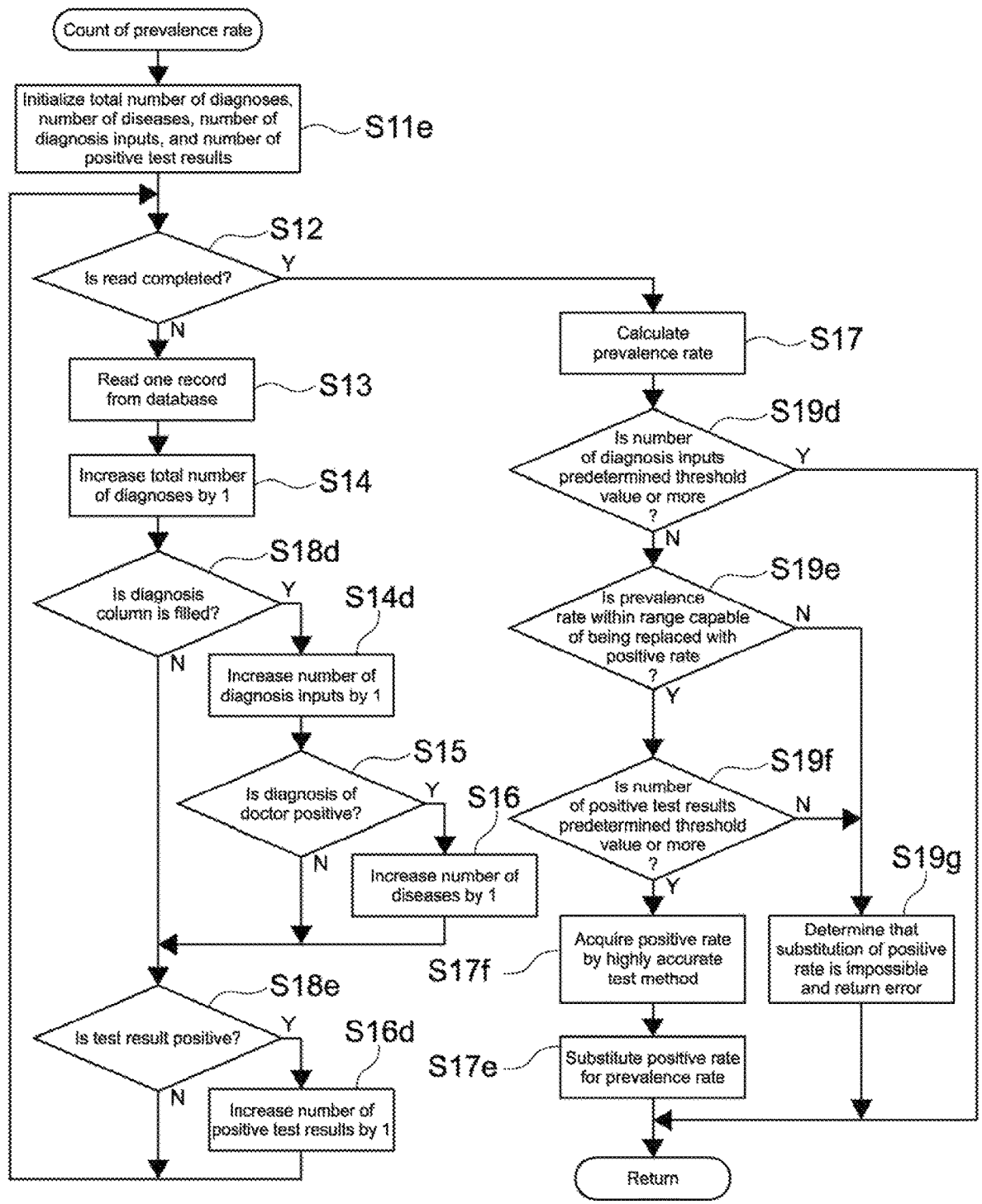
FIG. 21 is a flowchart for describing processing to count and calculate a prevalence rate in the case where the configuration of a modified example is adopted.

Here, processing to count and calculate a prevalence rate in the case where the configuration of this modified example is adopted will be described. FIG. 21 is a flowchart for describing processing to count and calculate a prevalence rate in the case where the configuration of this modified example is adopted.

It should be noted that this flowchart is almost the same as the flowchart in the modified example described above (identical thereto from Step S11e to Step S19f), in which a positive rate of a certain test method is substituted for a prevalence rate of the test method. In this regard, here, only a difference between the flowchart described above and a flowchart in this modified example will be described. The flowchart in this modified example shows processing in which a positive rate of a test method is substituted for a prevalence rate of a certain test method, the test method for the positive rate being more highly accurate (having higher sensitivity, higher specificity) than the test method for the prevalence rate.

In the case where the number of positive test results is a predetermined threshold value or more (Y of Step S19f), the CPU 41 then acquires a positive rate based on a highly accurate test method (Step S17f).

Next, the CPU 41 substitutes the positive rate for the prevalence rate (Step S17e). The positive rate based on a more highly accurate test method is substituted for the value of the prevalence rate and used in the following processing.

Hereinbefore, the modified example has been described in which a positive rate of a test method is substituted for a prevalence rate of a certain test method, the test method for the positive rate being more highly accurate (having higher sensitivity, higher specificity) than the test method for the prevalence rate.

It should be noted that in the case where results of a plurality of test methods on one disease are registered in the database 47a, a sensitivity and a specificity may be subjected to weighted average to obtain a comprehensive sensitivity and specificity, based on the number of registered records of the respective test methods. Further, a sensitivity and a specificity of one test method may be applied to all test methods registered in the database 47a. Further, test methods may be grouped and weighting may be performed for each of the groups, to obtain a comprehensive sensitivity and specificity. Furthermore, another index as a substitute for the prevalence rate has been described above, but a prevalence rate in an institution that is representative of its region can also be used instead of the prevalence rate based on the database 47a.

Modified Example 12 Presentation of Effectiveness on Implementation of Test

In the above configuration, the test terminal 20 presents information to a doctor who performs a test, the information being the prevalence rate, the positive predictive value, and the negative predictive value, that is, being a reference for the doctor who makes a final diagnosis. In contrast to this, in a modified example to be described here, for example, the test terminal 20 determines whether a calculated positive predictive value is a realistic value or not (evaluates the effectiveness) and if it is realistic (effective), the test terminal 20 recommends a doctor to perform a test.

It is useful when the doctor determines whether to execute a test or not to present, before the doctor executes a test, a probability (positive predictive value) that a positive result is obtained in a test and is truly positive and a probability (negative predictive value) that a negative result is obtained in a test and is truly negative, to the doctor.

Tests are always performed depending on a trade-off between side effects due to the execution of tests and costs of tests. For example, in the case where the prevalence rate is extremely low and the calculated positive predictive value is also too low to be realistic, a choice to perform no tests can be made.

As described above, in the case where the positive predictive value is too low to be realistic, the test terminal 20 can recommend execution of no tests, or in the case where the positive predictive value is sufficiently high, the test terminal 20 can recommend execution of tests, before performing tests.

Figure 22:
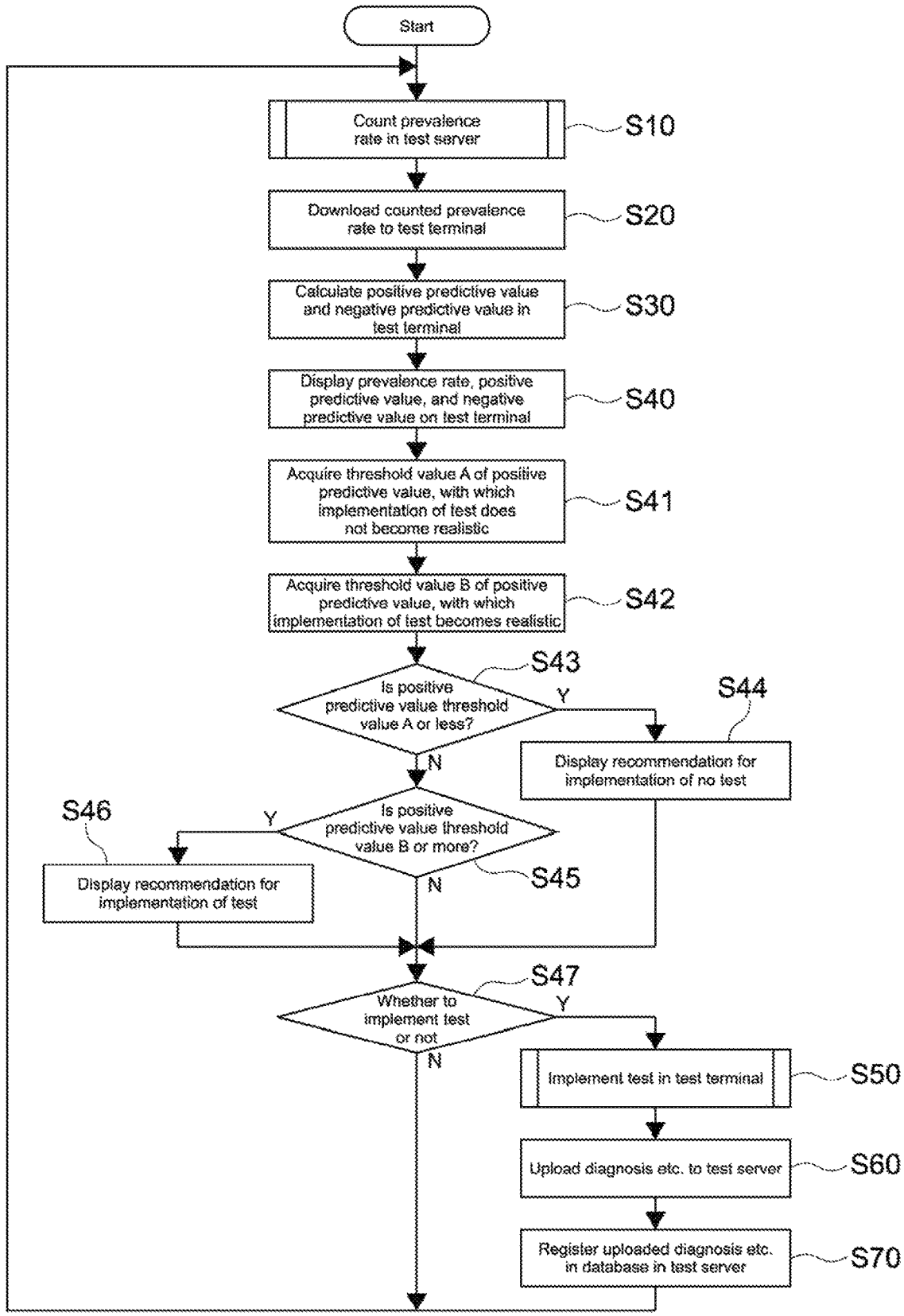
FIG. 22 is a flowchart of processing to recommend implementation of tests or implementation of no tests depending on the level of a calculated positive predictive value.

FIG. 22 is a flowchart of processing to recommend execution of tests or execution of no tests depending on the level of the calculated positive predictive value.

First, the CPU 41 of the test server 40 counts and calculates a prevalence rate for one disease and one test method using the database 47a in the test server 40 (Step S10).

Next, in the test terminal 20 with which a test will be implemented, the CPU 21 of the test terminal 20 downloads the prevalence rate calculated in the test server 40 (Step S20).

Next, in the test terminal 20 that downloads the prevalence rate, the CPU 21 calculates a positive predictive value and a negative predictive value (Step S30).

Next, the CPU 21 presents the prevalence rate, the positive predictive value, and the negative predictive value to a user or a doctor via the display unit 26 (Step S40).

Next, the CPU 21 acquires a threshold value A of the positive predictive value, with which implementation of a test does not become realistic (Step S41).

Next, the CPU 21 acquires a threshold value B of the positive predictive value, with which implementation of a test becomes realistic (Step S42). It should be noted that the threshold value A and the threshold value B may be preliminarily held in the test terminal 20, may be downloaded from the test server 40, or may be acquired from outside by another method.

Next, the CPU 21 determines whether the calculated positive predictive value is the threshold value A or less (Step S43).

In the case where the calculated positive predictive value is the threshold value A or less (Y of Step S43), the CPU 21 displays a recommendation for implementation of no tests to the user or doctor via the display unit 26 (Step S44).

In the case where the calculated positive predictive value is above the threshold value A (N of Step S43), the CPU 21 then determines whether the calculated positive predictive value is the threshold value B or more (Step S45).

In the case where the calculated positive predictive value is the threshold value B or more (Y of Step S45), the CPU 21 displays a recommendation for implementation of a test to the user or doctor via the display unit 26 (Step S46).

After the recommendation is displayed in Step S44 or Step S46 or in the case where the calculated positive predictive value is less than the threshold value B in Step S45 (N of Step S45), the CPU 21 then allows the doctor to determine whether to implement a test or not (Step S47).

In the case where the doctor determines implementation of a test and instructs the test terminal 20 to implement a test (Y of Step S47), a test is then implemented in the test device 28 of the test terminal 20 (Step S50).

Next, the CPU 21 uploads a diagnosis etc., which is input to the test terminal 20, to the test server 40 (Step S60).

Next, in the test server 40, the CPU 41 registers the uploaded information such as a diagnosis in the database 47a (Step S70).

After the registration in the database 47a in Step S70 or in the case where it is determined in Step S47 that a test is not implemented (N of Step S47), the processing returns back to Step S10 and the processing described above is repeated.

Hereinbefore, the modified example has been described in which the test terminal 20 determines whether the calculated positive predictive value is a realistic value or not, and if it is realistic, recommends the doctor to implement a test.

Modified Example 13 Prediction of Prevalence Rate in Region Where Test is not Implemented In the above description, past test results in a region where a test is implemented are counted, to calculate a prevalence rate in that region. In contrast to this, in a modified example to be described here, a prevalence rate in a region where a test is not previously implemented is predicted from prevalence rates calculated in other regions.

Figure 23:
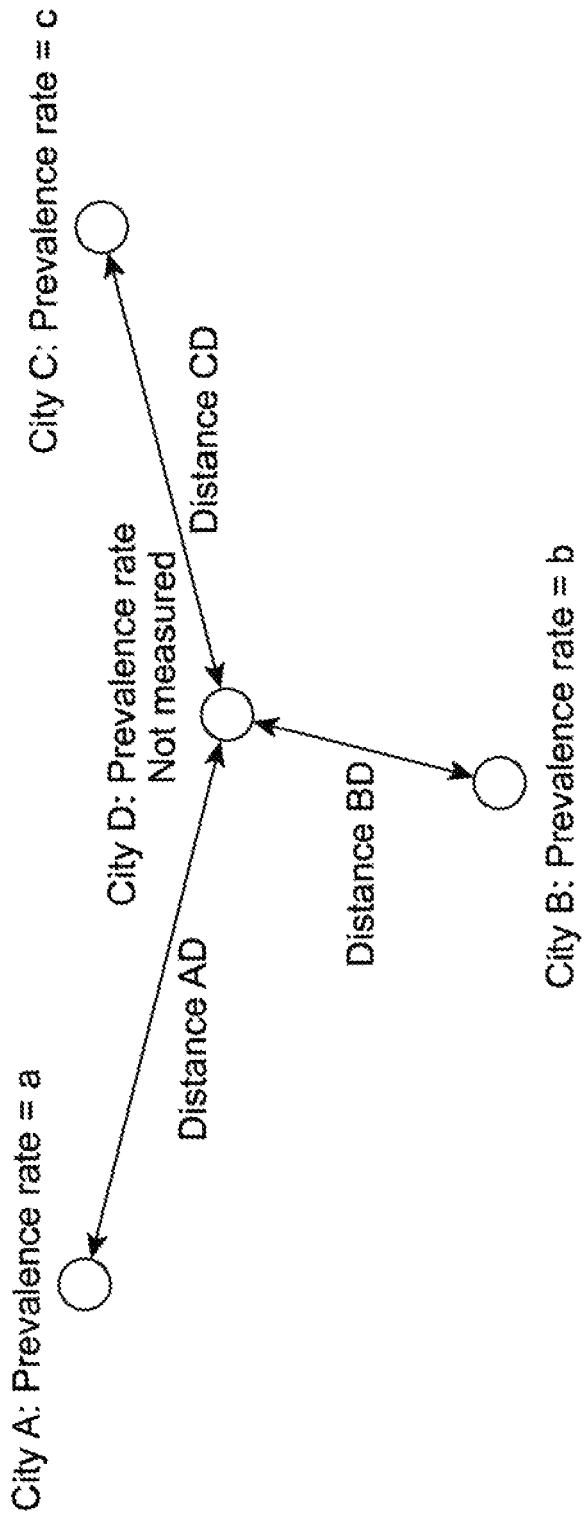
FIG. 23 is a diagram showing prevalence rates of a plurality of regions for which test results are already accumulated, and a state where a prevalence rate of a region where a test is not yet performed is predicted in accordance with distances from the plurality of regions.

FIG. 23 is a diagram showing prevalence rates of a plurality of regions for which test results are already accumulated, and a state where a prevalence rate of a region where a test is not yet performed is predicted in accordance with distances from the plurality of regions.

In this figure, tests have been implemented in the past in a city A, a city B, and a city C, for which test results are accumulated and a prevalence rate is calculated. In a city D, however, a test is not yet performed, and a prevalence rate cannot be calculated based on the count of the past test results. Here, when a distance between the cities A and D is denoted as a distance AD, a distance between the cities B and D is denoted as a distance BD, and a distance between the cities C and D is denoted as a distance CD, it is assumed that the prevalence rates of the cities A, B, and C and a prevalence rate of the city D to be predicted have a relationship shown by a mathematical expression in the figure.

The prevalence rates of the cities A, B, and C are obtained using the test terminal 20, distances between the cities are input to the test terminal 20, and the test terminal 20 is caused to perform a calculation based on the mathematical expression shown in the figure. This allows the prevalence rate of the city D to be predicted.

As described above, when a prevalence rate of a region where a test is not implemented can be predicted, for example, a guideline showing a region in which a mobile hospital or the like should perform a diagnosis or treatment next can be obtained.

It should be noted that here, a prevalence rate of a certain region is assumed to be inversely proportional to the square of a distance from another region. In addition thereto, the weighting correction may be performed based on a factor having an influence on infection, that is, at least one of a traffic situation between cities or a distance considering geographic features, a measurement time, a population density, and a medical level.

Hereinbefore, the modified example has been described in which the prevalence rate of a region where a test is not previously performed is predicted from prevalence rates calculated in other regions.

Modified Example 14 Prediction of Future Prevalence Rate

In the above description, the test system 10 provides a current prevalence rate. In contrast to this, in a modified example to be described here, a future predicted prevalence rate is also provided in addition to the current prevalence rate. It should be noted that processing to provide a future predicted prevalence rate may be performed in the test server 40 or in the test terminal 20, or may be shared between them. Here, description will be given on the assumption that the processing is performed in the test server 40.

Figure 24:
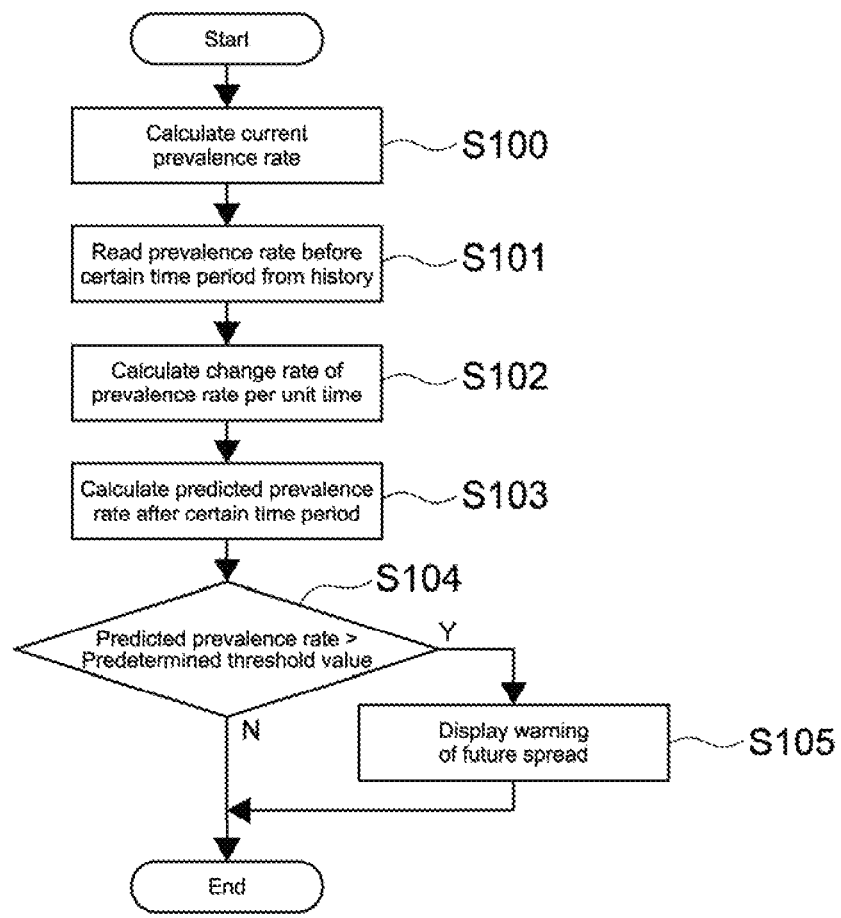
FIG. 24 is a flowchart for describing a processing flow to provide a future predicted prevalence rate as well, in addition to a current prevalence rate.

FIG. 24 is a flowchart for describing a processing flow to provide a future predicted prevalence rate as well, in addition to a current prevalence rate. In this processing, a future predicted prevalence rate after a certain time period is calculated based on a change rate of the prevalence rate during a certain time period up to the present. Further, in this processing, when a predicted prevalence rate exceeds a predetermined threshold value, warning is displayed. It should be noted that in this flowchart, only a part on processing to be described here is shown, and the step of storing a past prevalence rate, which is to be a precondition for the processing, as history information in the storage unit 47 is not described.

First, the CPU 41 of the test server 40 calculates a current prevalence rate (Step S100). This processing is performed by the method described above.

Next, the CPU 41 reads a prevalence rate before a certain time period, from history information of the storage unit 47 (Step S101). "Before certain time period" means before 24 hours, for example.

Next, the CPU 41 calculates a change rate of a prevalence rate per unit time, based on the prevalence rate before a certain time period and the current prevalence rate (Step S102). The change rate of the prevalence rate per unit time may be obtained by the following mathematical expression (18), for example.

(change rate of prevalence rate per unit time)=((current prevalence rate)−(prevalence rate before 24 hours))/24    (18)

It should be noted that in order to reduce a potential of erroneous processing due to temporal fluctuation of a prevalence rate, the following calculations may be performed:
(a) use an average of a plurality of prevalence rates that are acquired on a finer time basis (for example, every one hour) to serve as a current prevalence rate or a prevalence rate before a certain time period; and
(b) calculate change rates on a shorter time basis and obtain an average of those change rates.

Next, the CPU 41 calculates a predicted prevalence rate after a certain time period, based on the current prevalence rate and the change rate of the prevalence rate per unit time (Step S103). For example, the predicted prevalence rate after 24 hours may be calculated by the following mathematical expression (19).

(predicted prevalence rate after 24 hours)=(current prevalence rate)+(change rate per unit time)×24    (19)

Next, the CPU 41 determines whether the predicted prevalence rate exceeds a predetermined threshold value or not (Step S104).

Only in the case where the predicted prevalence rate exceeds a predetermined threshold value (Y of Step S104), the CPU 41 gives a warning of future infection spread to the user (Step S105). The warning given here may be given by any method. For example, the warning may be displayed on the display unit 26 of the test terminal 20 or may be given via e-mails, web pages on the Internet, and various types of SNS (Social Networking Service).

Hereinbefore, the modified example has been described in which the future predicted prevalence rate is also provided in addition to the current prevalence rate.

Modified Example 15 Optimization of Communication

In the above description, the configuration has been described in which information such as the prevalence rate is downloaded from the test server 40 each time a test is performed on the test terminal 20 side. In contrast to this, in this modified example, in order to reduce a load on the test server 40 and reduce communication charges between the test server 40 and the test terminals 20, the downloaded information such as the prevalence rate is cached in the test terminal 20. The test terminal 20 does not demand the test server 40 to provide information such as the prevalence rate each time a test is performed, but uses the information such as the prevalence rate cached in the test terminal 20 during a certain time period.

In the configuration of this modified example, the whole processing is roughly divided into two processing groups according to a frequency of the processing. One processing group is for processing performed on a predetermined certain-time-period basis, from count of the prevalence rate in the test server 40 to downloading of the prevalence rate, caching of the prevalence rate, and the like. The other processing group is for processing performed each time a test is performed, from reading of a cached prevalence rate and the like, to implementation of a test and reflection of a test result on the database 47*a*. It should be noted that the predetermined certain-time-period basis may be, for example, 30 minutes, 3 hours, or one day.

Figure 25:
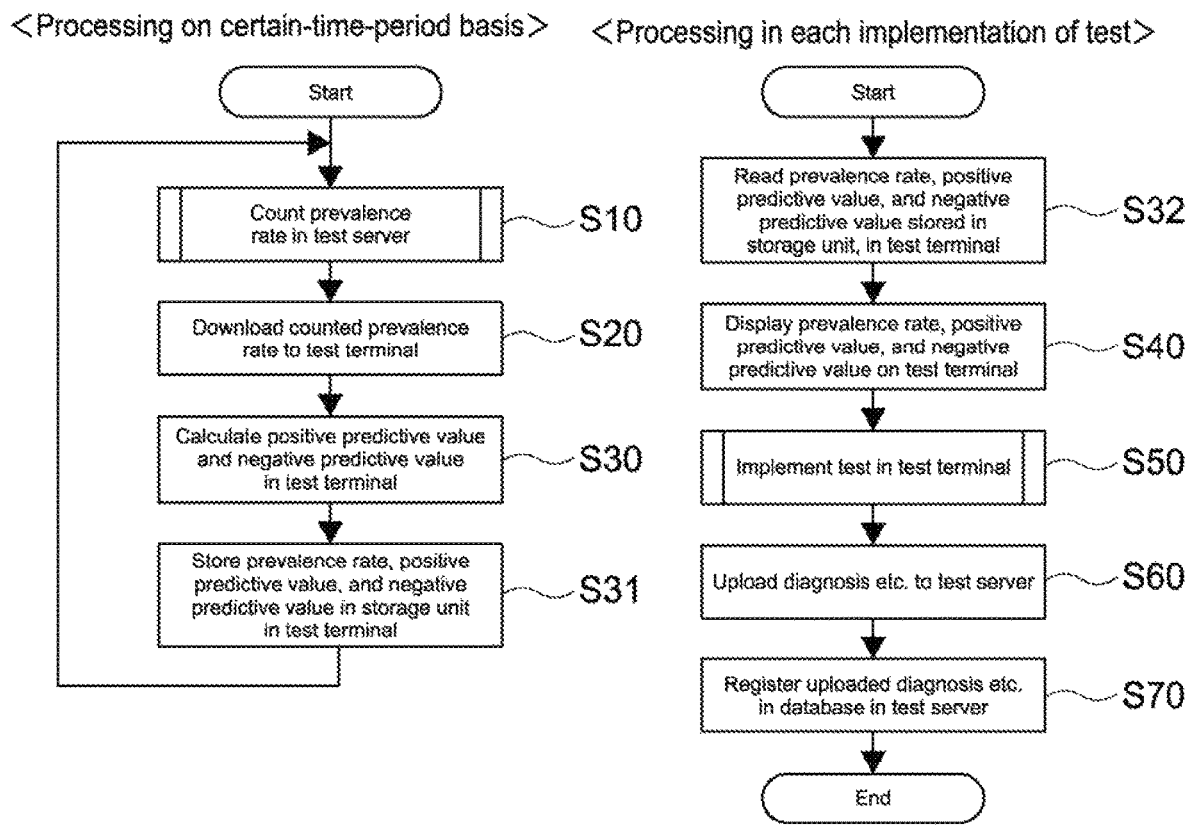
FIG. 25 is a flowchart showing processing on a predetermined certain-time-period basis and processing in each implementation of test.

FIG. 25 is a flowchart showing processing on a predetermined certain-time-period basis and processing in each implementation of test.

The processing on a certain-time-period basis will be described first. It should be noted that Steps S10 to S30 are the same as those described above, and thus simply described.

First, the CPU 41 of the test server 40 counts and calculates a prevalence rate using the database 47*a* in the test server 40 (Step S10).

Next, in the test terminal 20 in which information such as the prevalence rate is cached, the CPU 21 of the test terminal 20 downloads the prevalence rate calculated in the test server 40 (Step S20).

Next, in the test terminal 20 that downloads the prevalence rate, the CPU 21 calculates a positive predictive value and a negative predictive value (Step S30).

Next, the CPU 21 stores (caches) the downloaded prevalence rate and the calculated positive predictive value and negative predictive value in the storage unit 27 (Step S31).

After the processing of Step S31 is completed and a predetermined certain time period is elapsed, the processing is returned to Step S10 and repeated.

Hereinbefore, the processing flow on a certain-time-period basis has been described.

Next, the processing in each implementation of test will be described. It should be noted that Steps S40 to S70 are the same as those described above, and thus simply described.

First, the CPU 21 of the test terminal 20 reads a prevalence rate, a positive predictive value, and a negative predictive value from the cache in the storage unit 27 (Step S32).

Next, the CPU 21 presents the prevalence rate, the positive predictive value, and the negative predictive value to a user or a doctor via the display unit 26 (Step S40).

Next, in the test device 28 of the test terminal 20, a test is implemented according to an instruction of the user (Step S50).

Next, the CPU 21 uploads a diagnosis etc., which is input to the test terminal 20, to the test server 40 (Step S60).

Next, in the test server 40, the CPU 41 registers the uploaded information such as a diagnosis in the database 47*a* (Step S70).

Hereinbefore, the processing flow in each implementation of test has been described.

It should be noted that, as described above, in the case where information displayed by the test terminal 20 is only the prevalence rate, the positive predictive value, and the negative predictive value, the configuration of this modified example is effective because the cache size of the storage unit 27 is suppressed to be low. Further, also in the case where the modified example described above in which target data is narrowed down by patient attributes is applied, it is effective because of the same reason when the number of categories in a certain attribute is small. For example, in the case where a prevalence rate on a gender basis is cached, a prevalence rate to be stored includes only two types.

As described above, using the configuration of the modified example allows a reduction of a load of the test server 40 or a reduction of communication charges between the test server 40 and the test terminals 20, as compared with a configuration in which the prevalence rate and the like are counted in the test server 40 in each implementation of test and a count result is downloaded.

It should be noted that in the configuration described above, the test terminal 20 downloads information such as a prevalence rate on a certain-time-period basis, but the present technology is not limited thereto. For example, a configuration may be adopted, in which the test server 40 distributes a count result such as a prevalence rate to the test terminal 20 on a certain-time-period basis.

Hereinbefore, the modified example in which the downloaded information such as a prevalence rate is cached in the test terminal 20 has been described.

(Modified Example 16 Upload Form for Diagnosis Etc.)

In the above description, the configuration has been described in which the doctor inputs a final diagnosis etc. to the test terminal 20 and the test terminal 20 uploads the final diagnosis etc. to the test server 40. In contrast to this, in a modified example to be described here, a configuration will be described in which information such as a diagnosis is uploaded to the test server 40 via a local system such as an LIS (Laboratory Information System) in a hospital or a cloud system on the Internet.

Figure 26:
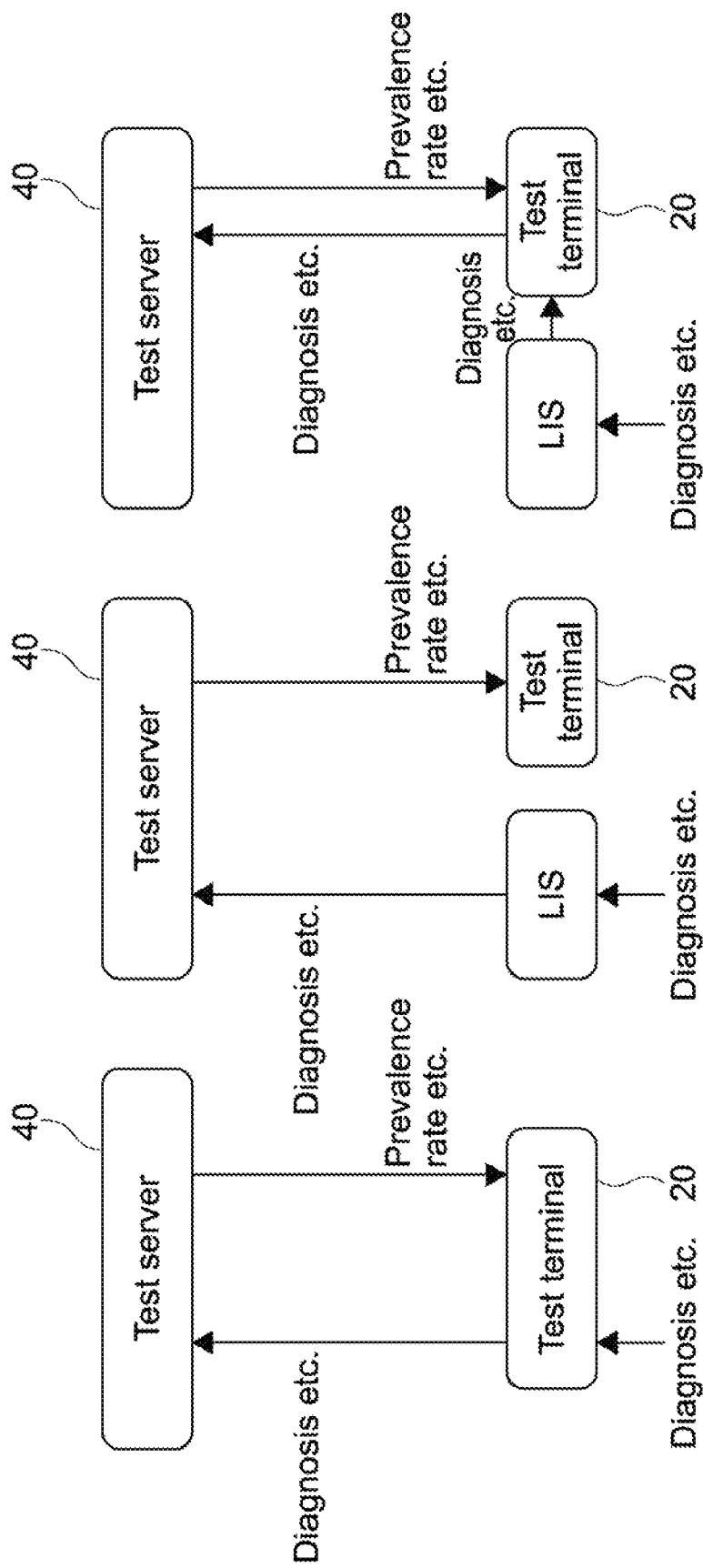
FIG. 26 is a diagram showing a configuration for uploading a diagnosis etc. using the LIS.

FIG. 26 is a diagram showing a configuration for uploading a diagnosis etc. using the LIS. The left part of the diagram shows a configuration in which a prevalence rate etc. are downloaded from the test server 40 and directly uploads a diagnosis etc. from the test terminal 20 to the test server 40. The configuration is described above. The center part of the diagram shows a configuration in which a doctor inputs a diagnosis to an LIS and the LIS uploads the diagnosis etc. to the test server 40. The right part of the diagram shows a configuration in which a doctor inputs a diagnosis to an LIS, the LIS transfers the diagnosis to the test terminal 20, and the test terminal 20 uploads the diagnosis to the test server 40.

It should be noted that though not shown in the figures, a configuration may be adopted in which a doctor inputs a final diagnosis to a system capable of accessing a wide range, such as a cloud system over the Internet, using a smartphone or a tablet PC, for example. In this case, the diagnosis etc. are transferred from the cloud system to the test server 40.

Hereinbefore, the modified example has been described in which the information such as a diagnosis is uploaded to the test server 40 via the local system such as an LIS in a hospital or the cloud system over the Internet.

Modified Example 17 Recommendation for Medication

In the above description, the configuration for presenting the calculated prevalence rate, positive predictive value, negative predictive value, and the like to a user or a doctor in the test terminal 20 has been described. In contrast to this, in a modified example to be described here, the test terminal 20 recommends medication to the user.

The recommendation for medication may be performed based on the level of the prevalence rate, the positive predictive value, and the negative predictive value, based on a result of an implemented test, or based on a final diagnosis of the doctor.

It should be noted that the recommendation for medication specifically refers to display of, for example, the presence or absence of the necessity of medication, a name of a medicine to be given, and a list of medicines to be medication candidates, on the display unit 26.

As a matter of course, in order to achieve the modified example, it is assumed that a knowledge base on diseases and medication is established in the test terminal 20, the test server 40, or outside the test system 10.

Hereinbefore, the modified example in which the test terminal 20 recommends medication to the user has been described.

Modified Example 18 User Interface

In the above description, the configurations for displaying, on the display unit 26 of the test terminal 20, a general prevalence rate, a prevalence rate as a result of narrowing-down by an attribute, a prevalence rate as a result of weighting, a positive rate as a substitute for the prevalence rate, recommendation for test implementation/non-implementation, a predicted prevalence rate, a recommendation for medication, a recommendation for individual management of patients, and the like have been individually described. In contrast to this, in a modified example to be described here, a configuration in which those displays are integrated will be described, for example.

FIG. 27 is a diagram showing a specific example in which a list of test methods feasible by the test device 28 of the test terminal 20 is presented on the test terminal 20 in addition to a name of a disease, a prevalence rate, a positive predictive value, and a negative predictive value, and a recommended test method is further displayed thereon.

In the figure, a PCR method is displayed with highlight together with a recommendation mark 26a. Further, beside each name of a test method, a UI (User Interface) such as a test start button 26b for instructing the test terminal 20 to start testing directly from this display screen is displayed. It should be noted that a UI for instructing a start of a test may have a configuration to give an instruction by a tracing operation or the like, in addition to a button.

Further, though not being a screen when information is presented, a screen displaying UIs for performing the following operations may be provided.

For example, a UI for giving an instruction to upload a test result to the test server 40 may be displayed on a screen displayed when a test is ended.

Further, instead of automatic uploading of a final diagnosis of a doctor to the test server 40, a UI for giving an instruction to upload a diagnosis to the test server 40 may be displayed on a screen indicating the input completion of the diagnosis.

Further, after the test is ended and a diagnosis etc. of the doctor are uploaded to the test server 40, a UI for giving an instruction to start the next test may be displayed on the screen.

Further, a UI for transferring to a screen for viewing statistical information such as the prevalence rate, the positive predictive value, and the negative predictive value may be provided on a screen displayed when the test is ended.

Further, after a final diagnosis of the doctor is input, it may be possible to display a screen on which various conditions for treatment desired by patients are input to the test terminal 20, to introduce hospitals and pharmacies corresponding to those conditions.

Further, after a final diagnosis of the doctor is input, it may be possible to display a screen on which treatment cost paid for treatment by a patient is input to the test terminal 20, to introduce a treatment method corresponding to the amount of treatment cost.

Hereinbefore, the modified example in which the displays are integrated, and the like, have been described.

Modified Example 19 Simplification of Test Terminal 20

In the above description, the configuration has been described in which the test system 10 adopts a client server configuration and the test terminal 20 as a client and the test server 40 as a server share processing. In contrast to this, in a modified example to be described here, a modified example will be described in which processing performed by the test terminal 20 is limited to minimum processing, and most processing is performed by the test server 40.

For example, the function of the test terminal 20 may be limited to display of information received from a test server, input of patient information etc., transmission of input data to the test server 40, execution of a test, display of a test result and transmission thereof to the test server 40, and input of a diagnosis of a doctor and transmission thereof to the test server 40.

The count, the calculation processing, the determination processing, and the like are performed by the test server 40, and thus the configuration of the test terminal 20 can be simplified and costs can be reduced.

Further, in this configuration, in the case where a new function is added, only the configuration of the test server 40 may be changed. The test terminal 20 does not need any change. Consequently, it is possible to omit time and effort for modifying many test terminals 20.

Hereinbefore, the modified example has been described in which the processing performed by the test terminal 20 is limited to minimum processing, and most processing is performed by the test server 40.

[Summary of Configurations of the Present Technology]

Here, the outline of the configurations and functions of the test system 10, the test server 40, and the test terminal 20 according to the present technology will be summarized.

The test server 40 according to the present technology includes the network interface unit 45 and the CPU 41. The network interface unit 45 communicates with the plurality of test terminals 20 via the network 30, the plurality of test terminals 20 each being connectable to a test device capable of executing a test on the presence or absence of a disease and each being capable of inputting a diagnosis on the presence or absence of the disease, the diagnosis being related to the test and made by a doctor. The CPU 41 acquires at least one of a result of the test and the diagnoses as a test information item from each of the plurality of test terminals 20 via the network interface unit 45, causes the storage unit 47 to store the plurality of acquired test information items therein, performs statistical processing on the plurality of stored test information items, and causes the network interface unit 45 to return a result of the statistical processing according to a demand given from each of the plurality of test terminals 20 before the doctor makes a diagnosis.

The test terminal 20 of the present technology includes the network interface unit 25, the operation input unit 24, and the CPU 21. The network interface unit 25 communicates with the test server 40 via the network 30, the test server 40 collecting a plurality of sets of at least one of a result of a test on the presence or absence of a disease and a diagnosis on the presence or absence of the disease as test information items, and providing a result of statistical processing performed on the plurality of collected test information items, the diagnosis being related to the test and made by a doctor. The operation input unit 24 receives an input from a user or the doctor. The CPU 21 causes the network interface unit 25 to transmit a demand of the result of the statistical processing to the test server 40, causes the test device 28 to execute the test, presents the result of the statistical processing and a result of the executed test to the user, the result of the statistical processing being received via the network interface unit 25 from the test server 40, causes the user to input the diagnosis on the executed test, using the operation input unit 24, and causes the network interface unit 25 to transmit at least one of the result of the executed test and the input diagnosis as the test information item to the test server 40.

The test system 10 of the present technology includes the test server 40 and the plurality of test terminals 20. The test server 40 includes the network interface unit 45 and the CPU 41. The network interface unit 45 communicates with the plurality of test terminals 20 via the network 30. The CPU 41 acquires at least one of a result of a test on the presence or absence of a disease and a diagnosis on the presence or absence of the disease as a test information item from each of the plurality of test terminals 20 via the network interface unit 45, the diagnosis being related to the test and made by a doctor, causes the storage unit 47 to store the plurality of acquired test information items therein, performs statistical processing on the plurality of stored test information items, and causes the network interface unit 45 to return a result of the statistical processing according to a demand given from each of the plurality of test terminals 20 before the doctor makes a diagnosis. The plurality of test terminals 20 each include the network interface unit 25, the operation input unit 24, and the CPU 21. The network interface unit 25 communicates with the test server 40 via the network 30. The operation input unit 24 receives an input from a user or the doctor. The CPU 21 causes the network interface unit 25 to transmit the demand of the result of the statistical processing to the test server 40, causes a test device to execute the test, presents the result of the statistical processing and a result of the executed test to the user, the result of the statistical processing being received via the network interface unit 25 from the test server 40, causes the user to input the diagnosis on the executed test, using the operation input unit 24, and causes the network interface unit 25 to transmit at least one of the result of the executed test and the input diagnosis as the test information item to the test server 40.

[Regarding Effects by the Embodiment]

By the test system 10 according to this embodiment, for example, the following effects can be obtained.

(1) Providing information to be indices for diagnosis, such as a prevalence rate, based on information acquired from many test terminals 20 can improve the degree of accuracy of a final diagnosis made by a doctor.

(2) Narrowing down and weighting information accumulated in the database 47a can further enhance the degree of accuracy of provided information such as a prevalence rate.

(3) Acquiring information that is not present in the test system 10 from outside can provide more useful information to a doctor, in addition to a prevalence rate and the like.

(4) Change only on the test server 40 side can provide new information based on a new function to a doctor.

(5) Unlike a typical test system, it is possible to cope with an infection and the like with instantaneity.

[Supplementary Note]

In addition, the present technology is not limited to the above embodiments and can be variously modified without departing from the gist of the present technology as a matter of course.

[Another Configuration of the Present Technology]

It should be noted that the present technology can have the following configurations.

(1) A test server, including:

communication unit that communicates with a plurality of communication terminals via a network, the plurality of communication terminals each being connectable to a test device capable of executing a test on the presence or absence of a disease and each being capable of inputting a diagnosis on the presence or absence of the disease, the diagnosis being related to the test and made by a doctor; and a control unit that acquires at least one of a result of the test and the diagnosis as a test information item from each of the plurality of communication terminals via the communication unit, causes a storage unit to store the plurality of acquired test information items therein, performs statistical processing on the plurality of stored test information items, and causes the communication unit to return a result of the statistical processing according to a demand given from each of the communication terminals before the doctor makes a diagnosis.

(2) The test server according to (1), in which the control unit causes the communication unit to return at least one of a prevalence rate, a positive predictive value, and a negative predictive value that are calculated as the result of the statistical processing, based on the number of test information items in which the result of the test and the diagnosis are positive, the number of test information items in which the result of the test is negative and the diagnosis is positive, the number of test information items in which the result of the test is positive and the diagnosis is negative, and the number of test information items in which the result of the test and the diagnosis are negative, in the plurality of stored test information items.

(3) The test server according to (2), in which the control unit causes the communication unit to return the positive predictive value and the negative predictive value, in addition to the prevalence rate, the positive predictive value and the negative predictive value being calculated based on the prevalence rate, a sensitivity of the test device, and a specificity of the test device.

(4) The test server according to (2) or (3), in which
the control unit
acquires, from each of the communication terminals, an elapsed time from the development of a disease of a patient who is to be subjected to the test,
acquires a sensitivity and a specificity that correspond to the elapsed time from the development of the disease, and
calculates the positive predictive value and the negative predictive value based on the acquired sensitivity and specificity.

(5) The test server according to any one of (1) to (4), in which
the control unit
causes the test device to execute various types of tests for testing the disease, the test device being connected to each of the communication terminals,
acquires results of the executed various types of tests from the test device, and
determines a result of the test indicating the presence or absence of the disease, based on the acquired results of the various types of tests.

(6) The test server according to any one of (1) to (4), in which
the test device is capable of executing various types of tests, and
the control unit calculates, after causing the test device to execute one of the various types of tests, posttest odds in the one test based on at least one of a positive likelihood ratio and a negative likelihood ratio on the one test, transmits the posttest odds to each of the communication terminals, and acquires information on whether a subsequent test is performed or not from each of the communication terminals (7) The test server according to any one of (1) to (6), in which
the test information items acquired from the communication terminals each include patient attribute information indicating an attribute of a patient who is subjected to the test, and
the control unit performs, when receiving a demand to narrow down statistical information from each of the communication terminals, the statistical processing by performing narrowing-down for test information items each having the attribute of the patient attribute information, the demand specifying any patient attribute information.

(8) The test server according to any one of (1) to (7), in which
the test information items acquired from the communication terminals each include terminal attribute information indicating an attribute of each of the communication terminals that performs the test, and
the control unit performs, when receiving a demand to narrow down statistical information from each of the communication terminals, the statistical processing by performing narrowing-down for test information items each having the attribute of the terminal attribute information, the demand specifying any terminal attribute information (9) The test server according to (8), in which
the control unit performs weighting on the result of the statistical processing, the weighting being based on the terminal attribute information, the result of the statistical processing being calculated based on the test information items obtained by narrowing-down.

(10) The test server according to any one of (2) to (4), in which
the control unit is capable of using a positive rate instead of the prevalence rate.

(11) The test server according to (10), in which
the test information item includes information for identifying a method of performing the test, and
the control unit is capable of using the positive rate instead of the prevalence rate in each of the methods of performing the test for an identical disease, the positive rate being the result of the statistical processing performed on a plurality of test information items acquired by one of the methods, the method satisfying preliminarily demanded predetermined values of a sensitivity and a specificity, out of sensitivities and specificities preliminarily provided to the respective methods, the prevalence rate being the result of the statistical processing performed on each of a plurality of test information items acquired by another one of the methods.

(12) The test server according to any one of (2) to (4), in which
the control unit evaluates effectiveness of the test based on the positive predictive value, transmits an evaluation result to each of the communication terminals, and causes each of the communication terminals to present a message of recommendation or non-recommendation for the test.

(13) The test server according to any one of (2) to (4), in which
the test information items acquired from the communication terminals each include information of a region in which each of the communication terminals is located, as terminal attribute information indicating an attribute of each of the communication terminals that performs the test, and
the control unit estimates the prevalence rate in a first region in which the test is not implemented, based on prevalence rates obtained in one or more second regions that are different from the first region, and based on a factor having an influence on infection between each of the second regions and the first region.

(14) The test server according to any one of (2) to (4), in which
the control unit periodically performs the statistical processing and creates history information of the prevalence rate, and predicts a future prevalence rate based on the history information.

(15) The test server according to any one of (1) to (14), in which
the control unit returns a result of the statistical processing acquired from outside, instead of performing the statistical processing on the plurality of stored test information items.

(16) The test server according to any one of (1) to (15), in which
the control unit transmits a list of medicines to each of the communication terminals, the medicines being based on at least one of the result of the test, the diagnosis, and the result of the statistical processing, and causes each of the communication terminals to present the list as medicines recommended for medication, or
the control unit causes each of the communication terminals to present a list of methods for the test capable of being performed in the test device, a recommendation mark indicating a method for a test recommended in the list, and a user interface for starting the test.

(17) A communication terminal, including:
a communication unit that communicates with a test server via a network, the test server collecting a plurality of sets of at least one of a result of a test on the presence or absence of a disease and a diagnosis on the presence or absence of the disease as test information items, and providing a result of statistical processing performed on the plurality of collected test information items, the diagnosis being related to the test and made by a doctor;

an input unit that receives an input from a user or the doctor; and a control unit that causes the communication unit to transmit a demand of the result of the statistical processing to the test server, causes a test device to execute the test, presents the result of the statistical processing and a result of the executed test to the user, the result of the statistical processing being received via the communication unit from the test server, causes the user to input the diagnosis on the executed test, using the input unit, and causes the communication unit to transmit at least one of the result of the executed test and the input diagnosis as the test information item to the test server.

(18) A test system, including:

a test server; and a plurality of communication terminals, the test server including a first communication unit that communicates with the plurality of communication terminals via a network, and a first control unit that acquires at least one of a result of a test on the presence or absence of a disease and a diagnosis on the presence or absence of the disease as a test information item from each of the plurality of communication terminals via the communication unit, the diagnosis being related to the test and made by a doctor, causes a storage unit to store the plurality of acquired test information items therein, performs statistical processing on the plurality of stored test information items, and causes the communication unit to return a result of the statistical processing according to a demand given from each of the communication terminals before the doctor makes a diagnosis, the plurality of communication terminals each including a second communication unit that communicates with the test server via the network, an input unit that receives an input from a user or the doctor, and a second control unit that causes the communication unit to transmit the demand of the result of the statistical processing to the test server, causes a test device to execute the test, presents the result of the statistical processing and a result of the executed test to the user, the result of the statistical processing being received via the communication unit from the test server, causes the user to input the diagnosis on the executed test, using the input unit, and causes the communication unit to transmit at least one of the result of the executed test and the input diagnosis as the test information item to the test server.

(19) A test method, including:

by a control unit, acquiring, from a plurality of communication terminals each being connectable to a test device capable of executing a test on the presence or absence of a disease and each being capable of inputting a diagnosis on the presence or absence of the disease, at least one of a result of the test and the diagnosis as a test information item via the communication unit, the diagnosis being related to the test and made by a doctor;

causing a storage unit to store the plurality of acquired test information items therein;

performing statistical processing on the plurality of stored test information items; and causing the communication unit to return a result of the statistical processing according to a demand given from each of the communication terminals before the doctor makes a diagnosis.

(20) A test method, including:

by a control unit, causing a communication unit to transmit a demand of a result of statistical processing to a test server, the communication unit communicating with the test server via a network, the test server collecting a plurality of sets of at least one of a result of a test on the presence or absence of a disease and a diagnosis on the presence or absence of the disease as test information items, and providing the result of the statistical processing performed on the plurality of collected test information items, the diagnosis being related to the test and made by a doctor;

causing the communication unit to transmit the demand of the result of the statistical processing to the test server;

causing a test device to execute the test;

presenting the result of the statistical processing and a result of the executed test to a user or the doctor, the result of the statistical processing being received via the communication unit from the test server;

causing the user to input the diagnosis on the executed test, using an input unit that receives an input from the user; and causing the communication unit to transmit at least one of the result of the executed test and the input diagnosis as the test information item to the test server.

DESCRIPTION OF SYMBOLS 10 test system
20 test terminal
21 CPU
22 ROM
23 RAM
24 operation input unit
25 network interface unit
26 display unit
27 storage unit
28 test device
30 network (Internet)
40 test server
41 CPU
42 ROM
43 RAM
44 operation input unit
45 network interface unit
46 display unit
47 storage unit
47a database

The invention claimed is:

1. A test server, comprising:
   circuitry configured to:
   communicate with a plurality of communication terminals via a network, wherein each of the plurality of communication terminals is connected to a test device
   that executes a test on one of a presence or an absence of a disease, each of the plurality of communication terminals inputs a diagnosis on the
   one of the presence or the absence of the disease, and the diagnosis is associated with the test and made by a doctor;
   acquire a plurality of test information items from the plurality of communication terminals, wherein each of the plurality of test information items comprises at least one of a result of the test or a result of the diagnosis;
   control a storage device to store the plurality of acquired test information items;
   perform statistical process on the plurality of stored test information items;
   output a result of the statistical process based on a demand given from each of the plurality of communication terminals before the diagnosis made by the doctor;
   acquire, from the test device, a current position of the test device and a position at which the test is performed;
   determine a prevalence rate based on a distance between the current position of the test device and the position at which the test is performed, wherein the prevalence rate is the result of the statistical process performed on each of the plurality of test information items acquired by a first method of a plurality of methods to perform the test; and
   output at least one of the prevalence rate, a positive predictive value, or a negative predictive value as the result of the statistical process based on:
      a number of at least one first test information item of the plurality of test information items in which the result of the test and the result of the diagnosis are positive;
      a number of at least one second test information item of the plurality of test information items in which the result of the test is negative and the result of the diagnosis is positive;
      a number of at least one third test information item of the plurality of test information items in which the result of the test is positive and the result of the diagnosis is negative; and
      a number of at least one fourth test information item of the plurality of test information items in which the result of the test and the result of the diagnosis are negative.

2. The test server according to claim 1, wherein the circuitry is further configured to calculate the positive predictive value and the negative predictive value based on the prevalence rate, a sensitivity of the test device, and a specificity of the test device.

3. The test server according to claim 2, wherein the circuitry is further configured to:
   acquire, from each of the plurality of communication terminals, an elapsed time from a development of the disease of a patient who is to be subjected to the test,
   acquire the sensitivity of the test device and the specificity of the test device that correspond to the elapsed time from the development of the disease, and
   calculate the positive predictive value and the negative predictive value based on the sensitivity and the specificity.

4. The test server according to claim 1, wherein the circuitry is further configured to:
   control the test device to execute a plurality of types of tests to test the disease, wherein the test device is connected to each of the plurality of communication terminals;
   acquire a plurality of results of the executed plurality of types of tests from the test device; and
   determine the result of the test that indicates the one of the presence or the absence of the disease, based on the plurality of results of the plurality of types of tests.

5. The test server according to claim 1, wherein the test device executes a plurality of types of tests, and
   the circuitry is further configured to calculate, after control of the test device to execute one of the plurality of types of tests, posttest odds in the test based on at least one of a positive likelihood ratio or a negative likelihood ratio on the test;
   transmit the posttest odds to each of the plurality of communication terminals; and
   acquire information on a subsequent test from each of the plurality of communication terminals.

6. The test server according to claim 1, wherein each of the plurality of test information items comprises patient attribute information that indicates an attribute of a patient who is subjected to the test, and
   the circuitry is further configured to perform, based on reception of the demand to narrow down statistical information from each of the plurality of communication terminals, the statistical process by narrow down of the plurality of test information items, wherein
      each of the plurality of test information items has the attribute of the patient attribute information, and
      the demand specifies the patient attribute information.

7. The test server according to claim 1, wherein each of the plurality of test information items comprises terminal attribute information that indicates an attribute of each of the plurality of communication terminals, and
   the circuitry is further configured to perform, based on reception of the demand to narrow down statistical information from each of the plurality of communication terminals, the statistical process by narrow down of the plurality of test information items, wherein
      each of the plurality of test information items has the attribute of the terminal attribute information, and
      the demand specifies the terminal attribute information.

8. The test server according to claim 7, wherein the circuitry is further configured to weight the result of the statistical process based on the terminal attribute information, and
   the result of the statistical process is based on the plurality of narrowed down test information items.

9. The test server according to claim 1, wherein the circuitry is further configured to:
   evaluate effectiveness of the test based on the positive predictive value;
   transmit an evaluation result to each of the plurality of communication terminals; and control each of the plurality of communication terminals to output a message of one of recommendation or non-recommendation for the test.

10. The test server according to claim 1, wherein
each of the plurality of test information items comprises information of a region in which each of the plurality of communication terminals is located,
the information is terminal attribute information that indicates an attribute of each of the plurality of communication terminals, and
the circuitry is further configured to estimate the prevalence rate in a first region in which the test is not implemented, based on a plurality of prevalence rates obtained in a plurality of second regions that are different from the first region, and based on a factor that has an influence on infection between each of the plurality of second regions and the first region.

11. The test server according to claim 1, wherein the circuitry is further configured to:
create history information of the prevalence rate based on the statistical process; and
predict a future prevalence rate based on the history information.

12. The test server according to claim 1, wherein the circuitry is further configured to output the result of the statistical process acquired from outside, instead of the statistical process on the plurality of stored test information items.

13. The test server according to claim 1, wherein the circuitry is further configured to:
transmit a list of medicines to each of the plurality of communication terminals, wherein the medicines are based on at least one of the result of the test, the diagnosis, or the result of the statistical process;
control each of the plurality of communication terminals to output the list of medicines recommended for medication; and
control each of the plurality of communication terminals to output at least one of a list of methods for the test, a recommendation mark that indicates a method for the test recommended in the list of methods for the test, or a user interface for starting the test.

14. A test system, comprising:
a test server; and
a plurality of communication terminals, wherein the test server comprises:
a first circuitry configured to:
communicate with the plurality of communication terminals via a network; and
acquire a plurality of test information items from each of the plurality of communication terminals, wherein
each of the plurality of test information items comprises a result of a test on one of a presence or an absence of a disease and a result of a diagnosis on the one of the presence or the absence of the disease, and
the diagnosis is associated with the test and made by a doctor;
control a storage device to store the plurality of acquired test information items;
perform statistical process on the plurality of stored test information items;
output a result of the statistical process based on a demand given from each of the plurality of communication terminals before the diagnosis made by the doctor;
acquire, from a test device, a current position of the test device and a position at which the test is performed;
determine a prevalence rate based on a distance between the current position of the test device and the position at which the test is performed, wherein the prevalence rate is the result of the statistical process performed on each of the plurality of test information items acquired by a method of a plurality of methods to perform the test; and
output at least one of the prevalence rate, a positive predictive value, or a negative predictive value as the result of the statistical process based on:
a number of at least one first test information item of the plurality of test information items in which the result of the test and the result of the diagnosis are positive;
a number of at least one second test information item of the plurality of test information items in which the result of the test is negative and the result of the diagnosis is positive;
a number of at least one third test information item of the plurality of test information items in which the result of the test is positive and the result of the diagnosis is negative; and
a number of at least one fourth test information item of the plurality of test information items in which the result of the test and the result of the diagnosis are negative, wherein
each of the plurality of communication terminals comprises:
a second circuitry configured to:
communicate with the test server via the network;
receive an input from at least one of a user or the doctor;
transmit the demand of the result of the statistical process to the test server;
control the test device to execute the test;
output the result of the statistical process and a result of the executed test to the user, wherein the result of the statistical process is received from the test server;
receive the diagnosis on the executed test based on an input from the user; and
transmit at least one of the result of the executed test and the input received diagnosis as the plurality of test information items to the test server.

15. A test method, comprising:
by a test server,
acquiring a plurality of test information items from a plurality of communication terminals, wherein
each of the plurality of communication terminals is connected to a test device that executes a test on one of a presence or an absence of a disease,
each of the plurality of communication terminals inputs a diagnosis of the one of the presence or the absence of the disease, and
the diagnosis is associated with the test and made by a doctor;
controlling a storage device to store the plurality of test information items;
performing statistical processing on the plurality of stored test information items;

outputting a result of the statistical processing based on a demand given from each of the plurality of communication terminals before the diagnosis made by the doctor;

acquiring, from the test device, a current position of the test device and a position at which the test is performed;

determining a prevalence rate based on a distance between the current position of the test device and the position at which the test is performed, wherein the prevalence rate is the result of the statistical processing performed on each of the plurality of test information items acquired by a method of a plurality of methods to perform the test; and outputting at least one of the prevalence rate, a positive predictive value, or a negative predictive value as the result of the statistical processing based on:
- a number of at least one first test information item of the plurality of test information items in which the result of the test and the result of the diagnosis are positive;
- a number of at least one second test information item of the plurality of test information items in which the result of the test is negative and the result of the diagnosis is positive;
- a number of at least one third test information item of the plurality of test information items in which the result of the test is positive and the result of the diagnosis is negative; and
- a number of at least one fourth test information item of the plurality of test information items in which the result of the test and the result of the diagnosis are negative.

\* \* \* \* \*